United States Patent
Padilla Iglesias et al.

(10) Patent No.: US 11,254,699 B2
(45) Date of Patent: Feb. 22, 2022

(54) PRODUCTION OF BIOMASS IN ULTRA HIGH DENSITY PLANTATIONS

(71) Applicant: DESERT KING CHILE S.A., Quinta Region (CL)

(72) Inventors: Leandro Padilla Iglesias, Quinta Region (CL); Javier Gonzalez Castro, Quinta Region (CL); Rodrigo Otero Peredo, San Diego, CA (US)

(73) Assignee: DESERT KING CHILE S.A., Quilpue (CL)

( * ) Notice: Subject to any disclaimer, the term of this patent is extended or adjusted under 35 U.S.C. 154(b) by 0 days.

(21) Appl. No.: 16/336,351

(22) PCT Filed: Sep. 26, 2016

(86) PCT No.: PCT/US2016/053724
§ 371 (c)(1),
(2) Date: Mar. 25, 2019

(87) PCT Pub. No.: WO2018/057031
PCT Pub. Date: Mar. 29, 2018

(65) Prior Publication Data
US 2019/0225637 A1   Jul. 25, 2019

(51) Int. Cl.
| | |
|---|---|
| *A61K 36/00* | (2006.01) |
| *C07H 1/08* | (2006.01) |
| *A01H 4/00* | (2006.01) |
| *A01H 6/00* | (2018.01) |
| *A01H 1/00* | (2006.01) |
| *C07H 15/256* | (2006.01) |

(52) U.S. Cl.
CPC ............... *C07H 1/08* (2013.01); *A01H 1/00* (2013.01); *A01H 4/005* (2013.01); *A01H 6/00* (2018.05); *C07H 15/256* (2013.01)

(58) Field of Classification Search
None
See application file for complete search history.

(56) References Cited

U.S. PATENT DOCUMENTS

2015/0141633 A1 * 5/2015 Goossens ............... C12P 15/00
536/23.2

OTHER PUBLICATIONS

Walther et al. (2011) Compendium on Detergency vol. 6(2): 20-22. (Year: 2011).*
Bull et al. (2000) Proc. Aus. Soc. Sugar Can Technol. No. 22, pp. 104-112. (Year: 2000).*
Wang et al. (2008) J. Chromatography A 1181: 51-59. (Year: 2008).*
Silvia Resnik; "Quillaia Extracts Type 1 and Type 2 Chemical and Technical Assessment (CTA)" Chemical and Technical Assessment; 61st JECFA; © FAO 2004; 9 pages.
Trinidad Schlotterbeck; et al., "The Use of Leaves from Young Trees of *Quillaja saponaria* (Molina) Plantations as a New Source of Saponins1", Economic Botany, XX(X), 2015, pp. 1-11, published online Sep. 29, 2015.
San Martin, Ricardo, et al.; "Industrial uses and sustainable supply of *Quillaja saponaria* (Rosaceae) saponins", Economic Botany v. 53 No. 3 (Jul./Sep. 1999) p. 302-11.
Sùren Kamstrupa,, et al; "Preparation and characterisation of quillaja saponin with less heterogeneity than Quil-A", Vaccine 18 (2000) 2244-2249.

* cited by examiner

*Primary Examiner* — Russell G Fiebig

(57) ABSTRACT

The present application relates to methods for the production of plant material suitable for the extraction and purification of saponins, through plantations of clone plants of defined chemotype, including ultrahigh density plantations of *Quillaja saponaria* Molina, and methods to increase the recovery of saponins by solid/liquid extraction of the harvested plant material.

4 Claims, 18 Drawing Sheets

PRODUCTION OF BIOMASS IN ULTRA HIGH DENSITY PLANTATIONS

BACKGROUND

Field

The present application relates to generating ultra-high-density plantations of *Quillaja* sp. to facilitate providing biomass for obtaining compounds from *Quillaja* The high-density plantations may be, but not limited to, clonally derived *Quillaja* sp.

Description of the Related Art

Saponins are compounds present in a wide variety of plants, having a chemical structure comprising a steroid or triterpenoid portion, attached to one or more sugar (saccharide) groups. The wide variety of chemical structures of saponins provides diverse physicochemical and biological characteristics, and therefore many industrial applications, such as in food, cosmetics, mining, agriculture, and pharmaceutical sectors.

To obtain products containing saponins, extraction and purification of these compounds from plant material is required. However, obtaining high-purity saponin extracts is technically difficult, both because of the diversity of saponin chemical structures, and because of the myriad of undesired compounds and impurities present in sources of saponins. For example, unwanted impurities include, but are not limited to phenolic compounds, proteins, carbohydrates and polysaccharides. The content of undesired impurities in the extract directly influences its industrial application. Indeed, the use of saponins in immunological applications requires a highly purified saponin, i.e., not containing any impurities that may adversely affect its pharmaceutical use.

There are various known methods for the purification of saponins, including solvent extraction, adsorption, ultrafiltration, or chromatography. For example, by using solubilizing compounds and exchange solvents, followed by dilution or dialysis. Similarly, impurities may be eliminated with adsorbents, followed by filtration, or through ultrafiltration, high performance liquid chromatography and reversed-phase chromatography.

However, the current purification methods are (i) not scalable to industrial levels; (ii) expensive; (iii) require excessively long periods for obtaining the purified saponins, and (iv) are not environmentally sustainable.

*Quillaja saponaria* produce a variety of saponins that are found mostly in the bark and to a lesser degree in woody tissue and leaves. See, e.g., *Chem. Tech. Assessment*, 61st JECFA. FAO (2004) and Econ. Bot., 69: 262-272. (2015). Importantly, each plant tissue contains a particular profile of saponin compounds. For example, the immunostimulant saponin QS-21 is mostly found in the inner bark of mature trees (i.e., trees at least 25 years old), with extremely low abundance in the woody tissue. Moreover, the saponins are not evenly distributed throughout the tree. For example, the saponin content of the bark is about 4% w/w, whereas only 1.6 % w/w is found in whole wood of the tree. See *Econ. Bot.*, 53: 302-311 (1999). The most abundant saponins of *Quillaja saponaria* are derivatives of the triterpenic aglycone qiuillaic acid, glycosidated at the $C_3$ and $C_{25}$ positions of the aglycone.

Historically, saponins are extracted from the bark and whole biomass of mature *Quillaja* trees growing wild in the forest. See *Econ. Bot.*, 69: 262-272 (2015). Wild *Quillaja* trees employed as source of raw materials for saponin production are at least 25 years old. This is problematic for saponin production, as the harvesting cycle is on the order of 15 years to be sustainable, and more typically 25-30 years for bark, or 10-12 years for pruning of twigs, leaves and branches. The current preferred manufacturing process including stripping the bark from wild trees in the spring months, transporting the bark to an extraction facility, and then drying, milling and extracting saponins from this bark.

The resulting extracts have a heterogeneous composition of saponins, i.e., different saponin profiles. However, there is a need to use saponins in their pure state (i.e. in pharmaceutical applications such as vaccine adjuvants). Accordingly, it would be beneficial for the *Quillaja* biomass employed as raw material to be chemically homogeneous (i.e., the biomass has a similar saponin profile) and must have high content of the desired saponin(s). For example, to purify the immunostimulant QS-21 by chromatography, it would be desirable to have a high content of QS-21 with only minor amounts of saponins eluting close to the target compound. However, obtaining large amounts of *Quillaja* biomass with a homogeneous saponin profile is technically difficult because of the chemical variability between trees growing in the wild, the uneven distribution of saponins in the tree, and the uncertain availability of the future supply of wild *Quillaja* biomass. Moreover, the selection of *Quillaja* trees for harvesting biomass is also technically difficult for the same reasons described above.

Current *Quillaja* cultivation methods do not address these issues. For example, these methods do not provide large amounts of *Quillaja* bark as the starting material for purification of saponins, nor provide any guidance regarding selection of which *Quillaja* trees to harvest and process. Indeed, the method proposed by Kamstnip et al., (2000) requires laborious procedures of sampling and chromatographic analysis of individual wild *Quillaja* trees before harvesting of homogeneous *Quillaja* bark suitable as raw material. Similarly, current methods do not improve the saponin composition of the biomass nor provide selection procedures before cultivation or harvesting of the *Quillaja* trees.

Accordingly, while *Quillaja* plantations of selected cultivars may facilitate increased saponin production and decrease the harvesting cycle time, the saponin content in the cultivated biomass as well as the productivity per hectare must be increased in order to be economically feasible. Moreover, the saponin content of wild trees is inconsistent, leading to sourcing issues.

SUMMARY

Some embodiments provide methods of making an enriched saponin compositions, comprising: (i) selecting *Quillaja* sp. plants based on chromatographic analysis of aqueous extracts of plant biomass for chemotype or total saponin content; (ii) removing axillary buds from said *Quillaja* sp. plants and inducing shoots of said axillary buds; (iii) growing apical meristems of the induced shoots to provide clone plantlets; (iv) growing said clone plantlets under controlled conditions to provide young plants; (v) transferring said young plants to an ultrahigh-density plantation; (vi) providing irrigation and nutrients to the young plants to provide young trees; (vii) harvesting the aerial biomass from the young trees; (viii) drying, grinding, and sieving said harvested biomass to provide biomass suitable for extraction; (ix) extracting said suitable biomass to provide an enriched saponin composition relative to that obtained from non-plantation biomass; and (x) repeating steps (vi)-(ix) about every year to about every 6 years.

some embodiments, the nutrients comprise a fertilizer. In some embodiments, the fertilizer comprises at least about 150 kg of nitrogen per hectare. In some embodiments the fertilizer comprises at least about 150 kg of nitrogen and about 100 kg of phosphorus per hectare, in some embodiments the fertilizer comprises at least about 150 kg of nitrogen, about 100 kg of phosphorus, and at least 150 kg of potassium per hectare. In some embodiments the fertilizer comprises between 150-250 kg of nitrogen, between 90-100 kg of phosphorus, and between about 150-250 kg of potassium per hectare. In some embodiments the fertilizer comprises at least about 200 kg of nitrogen, about 100 kg of phosphorus, and about 200 kg of potassium per hectare. In some embodiments the fertilizer comprises between 150-250 kg of nitrogen, between 90-100 kg of phosphorus, and between about 150-250 kg of potassium per hectare.

In some embodiments, steps (vi)-(ix) are repeated every year. In some embodiments, steps (vi)-(ix) are repeated every 2 years. In some embodiments, steps (vi)-(ix) are repeated every 3 years. In some embodiments, steps (vi)-(ix) are repeated every 4 years. In some embodiments, steps (vi)-(ix) are repeated every 5 years. In some embodiments, steps (vi)-(ix) are repeated every 6 years.

In some embodiments, the *Quillaja* sp. is *Quillaja saponaria* Molina. In some embodiments, the ultrahigh-density plantation comprises from about 20,000 plants per hectare to about 100,000 plants per hectare. In some embodiments, the *Quillaja* trees are planted a density of at least about 30,000 plants per hectare to about 100,000 plants per hectare. In some embodiments, the *Quillaja* trees are planted a density of at least about 40,000 plants per hectare to about 90,000 plants per hectare. In some embodiments, the *Quillaja* trees are planted a density of at least about 50,000 plants per hectare to about 80,000 plants per hectare. In some embodiments, the *Quillaja* trees are planted a density of at least about 60,000 plants per hectare to about 70,000 plants per hectare.

In some embodiments, the saponin composition is enriched for X-series saponins relative to non-plantation biomass. In some embodiments, the saponin composition is enriched for R-series saponins relative to non-plantation biomass. In some embodiments, the saponin composition is enriched by at least about 5% relative to non-plantation *Quillaja* sp. plants. In some embodiments, the saponin composition is enriched by at least about 10% relative to non-plantation *Quillaja* .sp. plants. In some embodiments, the saponin composition is enriched by at least about 15% relative to non-plantation *Quillaja* sp. plants.

Some embodiments provide methods of increasing the saponin content in harvestable *Quillaja* sp. biomass, comprising: (i) selecting *Quillaja* sp. plants based on chromatographic analysis of aqueous extracts of plant biomass for chemotype or total saponin content; (ii) removing axillary buds from said *Quillaja* sp. plants and inducing shoots of said axillary buds; (iii) growing apical meristems of the induced shoots to provide done plantlets; (iv) growing said clone plantlets under controlled conditions to provide young plants; (v) transferring said young plants to an ultrahigh-density plantation; (vi) providing irrigation and nutrients to the young plants to provide young trees; and (vii) harvesting the harvestable biomass from the young trees, In some embodiments, the harvestable biomass from said young trees is a larger percentage of total biomass than in non-plantation *Quillaja* sp. plants.

Some embodiments provide methods of increasing the saponin content of *Quillaja* sp. plants, comprising: (i) selecting *Quillaja* sp. plants based on chromatographic analysis of aqueous extracts of plant biomass for chemotype or total saponin content; (ii) removing axillary buds from said *Quillaja* sp. plants and inducing shoots of said axillary buds; (iii) growing apical meristems of the induced shoots to provide clone plantlets; (iv) growing said clone plantlets under controlled conditions to provide young plants; (v) transferring said young plants to an ultrahigh-density plantation; (vi) providing irrigation and nutrients to the young plants to provide young trees; and (vii) harvesting biomass from the young trees. In some embodiments, the biomass from said young trees has a higher saponin content than in non-plantation *Quillaja* sp. plants, and wherein the higher saponin content is selected from X-series saponins or R-series saponins.

Some embodiments provide methods for improving the saponin profile of *Quillaja* sp. plants comprising: (i) selecting *Quillaja* sp. plants based on chromatographic analysis of aqueous extracts of plant biomass for chemotype or total saponin content; (ii) removing axillary buds from said *Quillaja* sp. plants and inducing shoots of said axillary buds; (iii) growing apical meristems of the induced shoots to provide clone plantlets; (iv) growing said clone plantlets under controlled conditions to provide young plants; (v) transferring said young plants to an ultrahigh-density plantation; (vi) providing irrigation and nutrients to the young plants to provide young trees; and (vii) harvesting biomass from the young trees. In some embodiments, the biomass from said young trees has an improved saponin profile relative to non-plantation *Quillaja* sp. plants.

Some embodiments provide a *Quillaja* plantation comprising *Quillaja* trees planted at a density of at least about 500 plants per hectare to about 100,000 plants per hectare. In some embodiments, the *Quillaja* trees are cloned from a single tree. In some embodiments, the *Quillaja* trees are irrigated.

In some embodiments, the *Quillaja* trees are planted a density of at least about 1,000 plants per hectare to about 100,000 plants per hectare. In some embodiments, the *Quillaja* trees are planted a density of at least about 5,000 plants per hectare to about 90,000 plants per hectare. In some embodiments, the *Quillaja* trees are planted a density of at least about 10,000 plants per hectare to about 80,000 plants per hectare. In some embodiments, the *Quillaja* trees are planted a density of at least about 15,000 plants per hectare to about 70,000 plants per hectare. In some embodiments, the *Quillaja* trees are planted a density of at least about 20,000 plants per hectare to about 60,000 plants per hectare. In some embodiments, the *Quillaja* trees are planted a density of at least about 30,000 plants per hectare to about 50,000 plants per hectare.

In some embodiments, each *Quillaja* tree produces less than 50% R-series saponins. In some embodiments, each *Quillaja* tree produces less than 45% R-series saponins. In some embodiments, each *Quillaja* tree produces less than 40% R-series saponins. In some embodiments, each *Quillaja* tree produces less than 35% R-series saponins. In some embodiments, each *Quillaja* tree produces less than 30% R-series saponins. In some embodiments, each *Quillaja* tree produces less than 25% R-series saponins. In some embodiments, each *Quillaja* tree is substantially free of R-series saponins.

In some embodiments, each *Quillaja* tree produces less than 50% X-series saponins. In some embodiments, each *Quillaja* tree produces less than 45% X-series saponins. In some embodiments, each *Quillaja* tree produces less than 40% X-series saponins. In some embodiments, each *Quillaja* tree produces less than 35% X-series saponins. In some embodiments, each *Quillaja* tree produces less than 30% X-series saponins. In some embodiments, each *Quillaja* tree produces less than 25% X-series saponins. In some embodiments, each *Quillaja* tree is substantially free of X-series saponins.

Some embodiments provide a *Quillaja* biomass comprising not more than about 50% R-series saponins, wherein the biomass is harvested from at least about 50 *Quillaja* trees. In some embodiments, the biomass is harvested from at least about 100 *Quillaja* trees. In some embodiments, the biomass is harvested from at least about 500 *Quillaja* trees. In some embodiments, the biomass comprises not more than about 45% R-series saponins. In some embodiments, the biomass comprises not more than about 40% R-series saponins. In some embodiments, the biomass comprises not more than about 35% R-series saponins. In some embodiments, the biomass comprises not more than about 25% R-series saponins. In some embodiments, the biomass is substantially free of R-series saponins. In some embodiments, the *Quillaja* trees are clonal. In some embodiments, the *Quillaja* trees are cloned from a single tree.

Some embodiments provide a *Quillaja* biomass comprising not more than 50% X-series saponins, wherein the biomass is harvested from at least about 50 *Quillaja* trees. In some embodiments, the biomass is harvested from at least about 100 *Quillaja* trees. In some embodiments, the biomass is harvested from at least about 500 *Quillaja* trees. In some embodiments, the biomass comprises not more than about 45% X-series saponins. In some embodiments, the biomass comprises not more than about 40% X-series saponins. In some embodiments, the biomass comprises not more than about 35% X-series saponins. In some embodiments, the biomass comprises not more than about 30% X-series saponins. In some embodiments, the biomass is substantially free of X-series saponins. In some embodiments, the *Quillaja* trees are clonal. In some embodiments, the *Quillaja* trees are cloned from a single tree.

In some embodiments, the *Quillaja* trees are planted a density of at least about 1,000 plants per hectare to about 100,000 plants per hectare. In some embodiments, the *Quillaja* trees are planted a density of at least about 5,000 plants per hectare to about 90,000 plants per hectare. In some embodiments, the *Quillaja* trees are planted a density of at least about 10,000 plants per hectare to about 80,000 plants per hectare. In some embodiments, the *Quillaja* trees are planted a density of at least about 15,000 plants per hectare to about 70,000 plants per hectare. In some embodiments, the *Quillaja* trees are planted a density of at least about 20,000 plants per hectare to about 60,000 plants per hectare. In some embodiments, the *Quillaja* trees are planted a density of at least about 30,000 plants per hectare to about 50,000 plants per hectare.

Some embodiments provide a crude extract of *Quillaja* trees, wherein the extract comprises not more than 5% R-series saponins, and wherein the extract is obtained from at least about 50 *Quillaja* trees. In some embodiments, the *Quillaja* trees are clonal. In some embodiments, the *Quillaja* trees are cloned from a single tree.

In some embodiments, the extract comprises not more than 50% R-series saponins. In some embodiments, the extract comprises not more than 40% R-series saponins. In some embodiments, the extract comprises not more than 30% R-series saponins. In some embodiments, the extract comprises not more than 25% R-series saponins. In some embodiments, the extract is substantially free of R-series saponins.

In some embodiments, the extract comprises not more than 50% X-series saponins, and wherein the extract is obtained from at least about 50 *Quillaja* trees. In some embodiments, the extract comprises not more than 45% X-series saponins. In some embodiments, the extract comprises not more than 40% X-series saponins. In some embodiments, the extract comprises not more than 35% X-series saponins. In some embodiments, the extract comprises not more than 30% X-series saponins. In some embodiments, the extract is substantially free of X-series saponins.

In some embodiments, the extract is obtained from at least about 100 *Quillaja* trees. In some embodiments, the extract is obtained from at least about 500 *Quillaja* trees. In some embodiments, the *Quillaja* trees are clonal. In some embodiments, the *Quillaja* trees are clonal. In some embodiments, the *Quillaja* trees are cloned from a single tree. For exemplary methods of extraction and purification of saponins from *Quillaja*, see for example PCT/CL2015/000062, the contents of which are hereby incorporated by reference in their entirety, including any drawings.

In some embodiments, the *Quillaja* trees are planted a density of at least about 1,000 plants per hectare to about 100,000 plants per hectare. In some embodiments, the *Quillaja* trees are planted a density of at least about 5,000 plants per hectare to about 90,000 plants per hectare. In some embodiments, the *Quillaja* trees are planted a density of at least about 10,000 plants per hectare to about 80,000 plants per hectare. In some embodiments, the *Quillaja* trees are planted a density of at least about 15,000 plants per hectare to about 70,000 plants per hectare. In some embodiments, the *Quillaja* trees are planted a density of at least about 20,000 plants per hectare to about 60,000 plants per hectare. In some embodiments, the *Quillaja* trees are planted a density of at least about 30,000 plants per hectare to about 50,000 plants per hectare.

DETAILED DESCRIPTION

Figure 1:
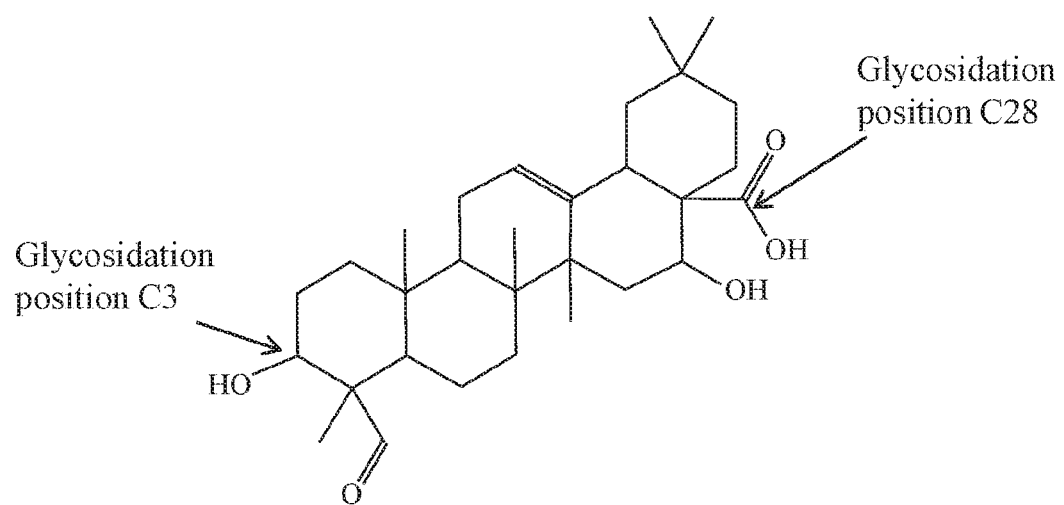
FIG. 1 depicts the chemical structure of quillaic acid and notes the glycosidation sites at the $C_3$ and $C_{28}$ positions.
Figure 2:
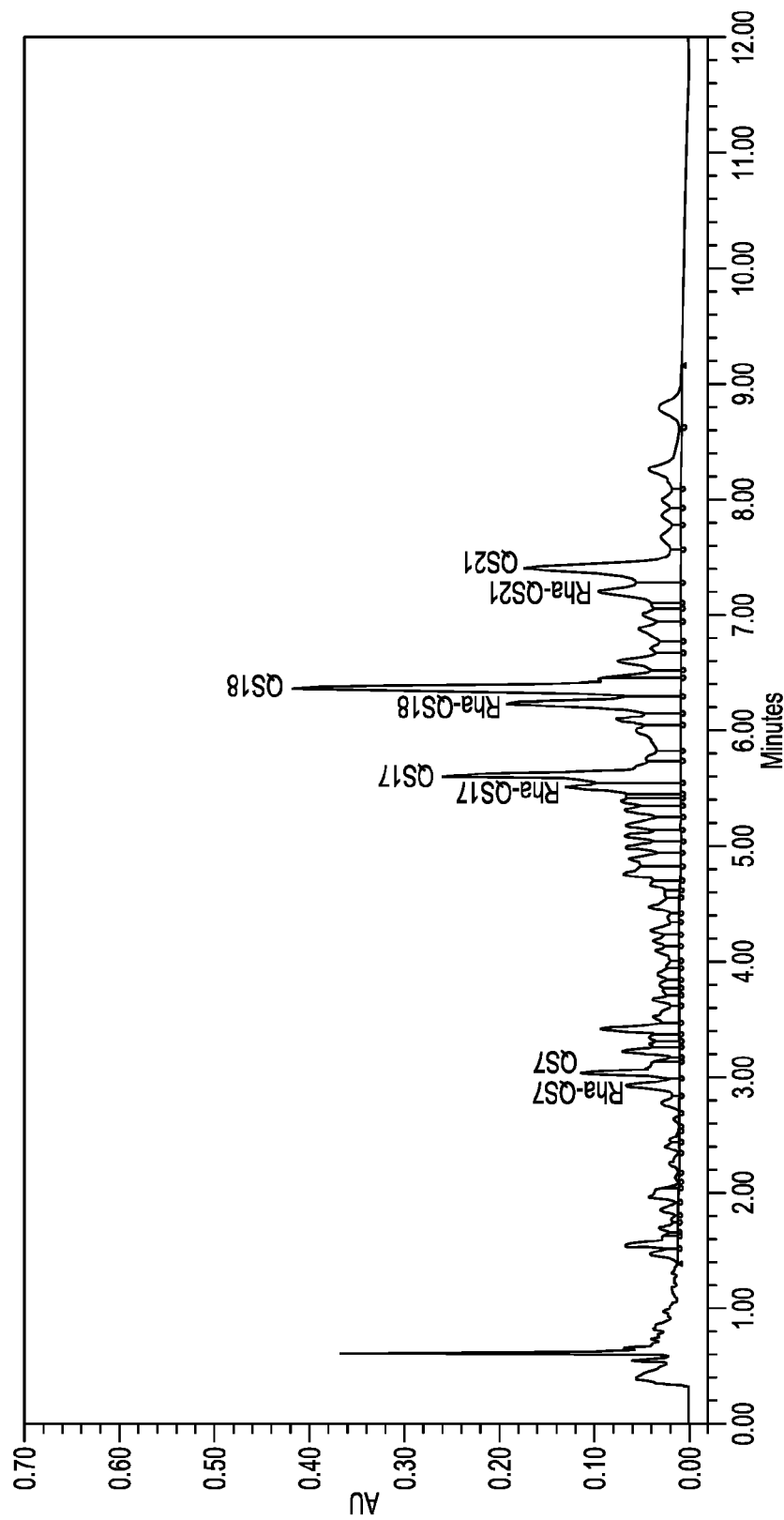
FIG. 2 shows a representative reverse phase UHPLC chromatogram of an extract of the bark of *Quillaja saponaria* Molina, including the most abundant saponins in the X-series (QS-7, QS-17, QS-18, QS21), as well as the corresponding saponins in the R-series (Rha-QS-7, Rha-QS-17, Rha-QS-18 and Rha-QS21).

The present application is directed to the development of agricultural methods to increase the saponin content in the biomass of *Quillaja* sp. grown in plantations. Further, using clonally-derived trees in such plantations will increase the consistency of the saponin profile in the resulting extracts, providing more predictable results and streamlining purification of the saponin extracts.

The present application is also directed to the sustainable production of large amounts of *Quillaja* sp. biomass, for example *Quillaja saponaria* Molina, for the extraction of saponins. Although described primarily in reference to *Quillaja saponaria* Molina, unless otherwise indicated other varieties can be used, as would be apparent to the skilled artisan. The present disclosure provides a practical, sustainable, and economically viable alternative to the current methods of saponin production.

Some embodiments provide methods for providing *Quillaja saponaria* Molina biomass containing saponins of the X-series and substantially free of saponins of the R-series. Some embodiments provide methods for providing *Quillaja* sp. biomass containing saponins of the R-series and substantially free of saponins of the X-series.

Some embodiments provide methods for providing *Quillaja saponaria* Molina trees containing saponins of the X-series and substantially free of saponins of the R-series. Some embodiments provide methods for providing *Quillaja* sp. trees containing saponins of the R-series and substantially free of saponins of the X-series.

Some embodiments provide methods for obtaining homogeneous biomass from *Quillaja saponaria* Molina comprising the steps of: planting clone plants of *Quillaja saponaria* Molina of the same saponin chemotype in an ultrahigh-density plantation (surface density, _000-100,000 plants/hectare), providing irrigation and nutrients to the planted plants, growing the plants to young trees, harvesting parts of the grown trees, drying, chipping and sieving of the harvested biomass to obtain chipped twigs of *Quillaja saponaria* Molina.

Some embodiments provide methods of selecting *Quillaja saponaria* Molina biomass containing saponins of the X-series and substantially free of saponins of the R-series, or selecting *Quillaja saponaria* Molina containing saponins of the R-series and substantially free of saponins of the X-series, cloning of the selected *Quillaja* trees, industrial cultivation of the resulting clones, harvesting of the cultivated biomass, extraction of the saponins from the harvested biomass, purification of the extracted saponins and/or chemical modification of the extracted saponins. In some embodiments, the bark is substantially free of R-series saponins, the leaves are substantially free of R-series saponins, the stems are substantially free of R-series saponins, the roots are substantially free of R-series saponins, the seeds are substantially free of R-series saponins, the flowers are substantially free of R-series saponins, the fruit is substantially free of R-series saponins, or any combination thereof, is substantially free of R-series saponins. In some embodiments, the entire plant is substantially free of R-series saponins, in some embodiments, the aerial biomass is substantially free of R-series saponins. In some embodiments, the hark is substantially free of X-series saponins, the leaves are substantially free of X-series saponins, the stems are substantially free of X-series saponins, the roots are substantially free of X-series saponins, the seeds are substantially free of X-series saponins, the flowers are substantially free of X-series saponins, the fruit is substantially free of X-series saponins, or any combination thereof, is substantially free of X-series saponins. In some embodiments, the entire plant is substantially free of X-series saponins. In some embodiments, the aerial biomass is substantially free of X-series saponins.

The term "young plant," as used herein, refers to plants grown in a nursery that are 0-3 years old. The term "young tree," as used herein, refers to plants not more than about 20-25 years old.

The terms "mature plant" and "mature tree," as used herein, refer to plants at least about 25 years old.

The term "controlled conditions," as used herein refers to an environment for plant growth, for example a nursery or greenhouse, where at least temperature, and preferably temperature and humidity, may be modified relative to the external environment.

The term "*Quillaja* sp.," as used herein, refers to *Quillaja saponaria* Molina.

The term "biomass," as used herein, refers to any biological material originated from the kingdom Planiae. For example, the biomass can be the bark, trunk, leaves, stems, roots, seeds, flowers, fruits or a combination of any of them. In some embodiments, whole-plant biomass is used. "Whole-plant biomass" refers to at least that portion of the plant above the root (i.e., the trunk or stem, on up). In some embodiments, biomass comprises the bark, trunk, leaves, stems, roots, seeds, flowers, and/or fruits. In some embodiments, the biomass is bark. In some embodiments, the biomass is obtained from clonally grown whole plants. In some embodiments, the biomass comprises bark, trunk, leaves, stems, roots, seeds, flowers, and/or fruits of clonally grown whole plants. In some embodiments, the biomass is bark from clonally grown whole plants.

The term "harvestable biomass," as used herein refers to plant biomass that may be cyclically harvested (i.e., removed from the plant) without substantially harming the plant and/or inhibiting its growth. In contrast, non-harvestable biomass refers to biomass that cannot be harvested without substantially harming the plant and/or inhibiting its growth, for example, the trunk or root system.

The term "medium-density plantation," as used herein, refers to plantations containing at least about 500 to not more than about 2,000 plants per hectare.

The term "high-density plantation," as used herein, refers to plantations containing at least about 2,000 to not more than about 20,000 plants per hectare.

The term "ultrahigh-density plantation," as used herein, refers to plantations containing at least about 20,000 *Quillaja* plants per hectare, up to over 100,000 *Quillaja* plants per hectare.

The term "saponin," as used herein, refers to as any glycoside characterized in that it comprises insoluble hydrophobic portion comprising a steroid or triterpenoid, and a hydrophilic portion comprising one or more saccharide chains. The saccharides can be any sugar, including, but not limited to glucose, arabinose, galactose, rhamnose, xylose, fucose, xylose, sucrose, lactose, maltose, trehalose, cellobiose, chitobiose, isomaltose, sophorose, sorbitol, mannitol, glucuronic acid and galacturonic acid.

The term "substituent X," as used herein, refers to a β-D-galactopyranosyl-(1→2)-[β-D-xylopyranosyl-(1→3)]-β-D-glucuronopyranosyl unit attached to the position of the aglycone portion of a saponin.

The term "substituent R," as used herein refers to a β-D-galactopyranosyl-(1→2)-[α-L-rhamnopyranosyl-(1→3)]-β-D-glucuronopyranosyl unit attached to the $C_3$ position of the aglycone portion of a saponin.

The term "X-series," as used herein, refers to saponins with substituent at the $C_3$ position of the aglycone.

The term "R-series," as used herein, refers to saponins with substituent R at the $C_3$ position of the aglycone.

The term "chemotype," as used herein, refers to the predominance of the X-series or R-series saponins produced by the plant.

The term "homogeneous," as used herein, refers to (i) saponin compositions and/or saponin profiles, containing a defined series, either X or R, and substantially free of the saponins belonging to the alternative series, and also (ii) populations of *Quillaja* sp. that have a similar saponin profile. For example, a homogenous X-series composition is substantially free of R-series saponins, and a homogenous R-series composition is substantially free of X-series saponins. Likewise, a homogenous population of chemotype X *Quillaja saponaria* Molina has a saponin profile containing a defined series, either X or R, and substantially free of the saponins belonging to the alternative series.

The term "substantially free," as used herein, refers to a saponin composition containing less than 20% of a particular saponin (or class of saponins). For example, a saponin composition that is substantially free of R-series saponins contains predominantly X-series saponins, with less than 20% R-series saponins.

Figure 3:
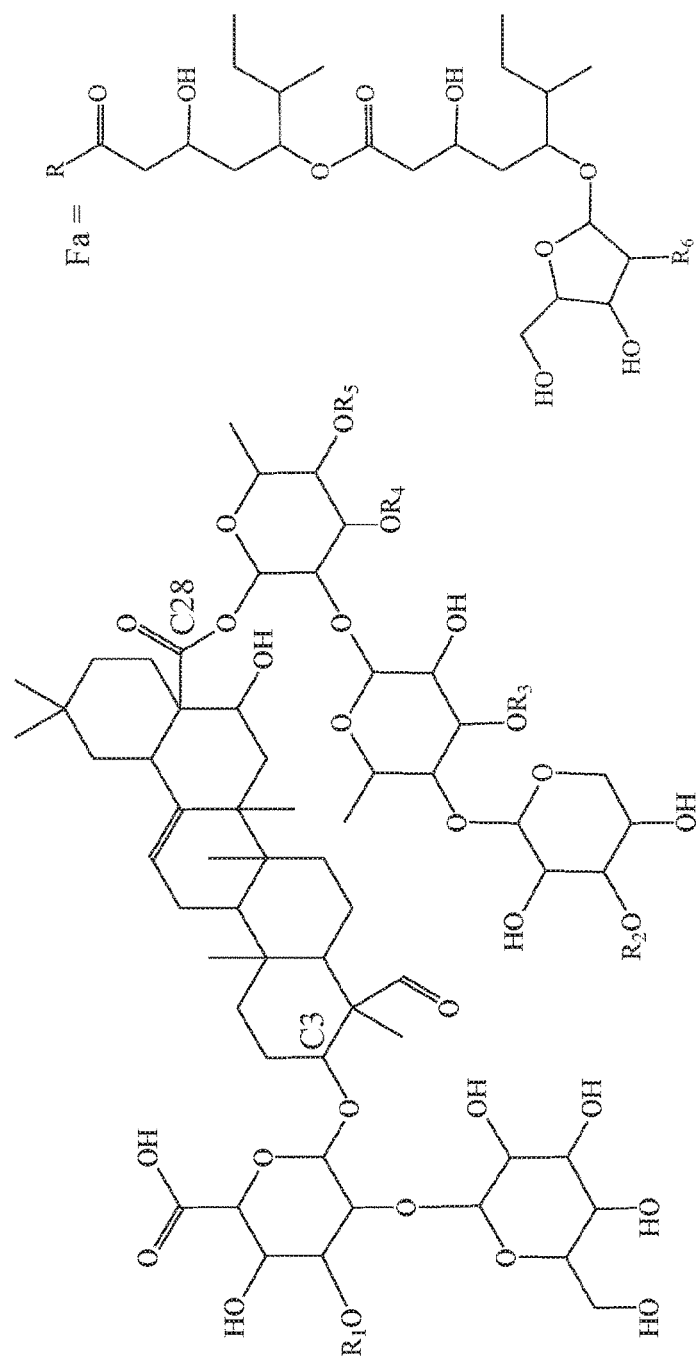
FIG. 3 depicts the chemical structures of the most abundant saponins of *Quillaja saponaria* belonging to the X-series (QS-7, QS-17, QS-18, QS21), as well as the corresponding saponins in the R-series (Rha-QS-7, Rha-QS-17, Rha-QS-18 and Rha-QS21).

The term "QS-21," as used herein, refers to the compound 4 in the FIG. 3.

The term "QS-18" as used herein, refers to the compound 3 in the FIG. 3.

The term "QS-17" as used herein, refers to the compound 2 in the FIG. 3

The term "Rha-QS-21," as used herein refers to the R-series analog of QS-21, with substituent R at the $C_3$ position, referred as compound 8 in the FIG. 3.

The term "Rha-QS-18," as used herein refers to the R-series analog of QS-18, with substituent Rat the $C_3$ position, referred as compound 7 in the FIG. 3.

The term "Rha-QS-17," as used herein refers to the R-series analog of QS-17, with substituent Rat the $C_3$ position, referred as compound 6 in the FIG. 3.

The term "aerial biomass," as used herein refers to the parts of the plant that do not directly contact the ground, including, but not limited to, branches, twigs, leaves, and sections of the stem not in contact with the ground.

The term "vigor," as used herein refers to the hardiness of a plant, as measure by the height of the plant, the diameter of the root collar of the plant, or both.

In some embodiments, the *Quillaja* sp. for cultivation comprises seedlings or young plants propagated from seeds collected as seeds, seedlings, clonally from tissues, or in nurseries, seedlings or young plants propagated clonally from tissues of *Quillaja* trees selected by their vigor, their saponin composition, their total saponin content, or a combination of the aforementioned traits.

The term "crude extract," as used herein, refers to an extract of plant biomass that has not been purified, but has optionally been concentrated.

Some embodiments provide methods for selecting and propagating *Quillaja* plants of a defined saponin chemotype, comprising the steps of: selecting parental trees by chromatographic analysis of aqueous extracts of sampled plant biomass, for example, bark and/or pruned branches and/or twigs, removal of axillary buds from said parental trees, inducing the shoots of said axillary buds in vitro, growing apical meristems of the induced shoots to provide plantlets, and transferring the plantlets to a nursery to provided clone plants of *Quillaja* with a defined saponin chemotype.

Some embodiments provide methods of increasing the saponin content of *Quillaja* sp. biomass from a plantation. In some embodiments, the method comprises selecting parental trees by chromatographic analysis of aqueous extracts of sampled plant biomass, for example, bark and/or branches, removal of axillary buds from said parental trees, inducing the shoots of said axillary buds in vitro, growing apical meristems of the induced shoots to provide plantlets, and transferring the plantlets to a nursery to provided clone plants of *Quillaja* with an increased saponin content relative to pooled extracts of non-plantation *Quillaja'bpi sp.*

Some embodiments provide methods of selecting *Quillaja* sp. for cultivation. In some embodiments, the method comprises selecting *Quillaja* sp. for cultivation in high-density plantations. In some embodiments, the method comprises selecting *Quillaja* sp. for cultivation in ultrahigh-density plantations. In some embodiments, the method comprises selecting parental trees by chromatographic analysis of aqueous extracts of sampled plant biomass, for example, bark and/or branches, and/or twigs, removal of axillary buds from said parental trees, inducing the shoots of said axillary buds in vitro, growing apical meristems of the induced shoots to provide plantlets, and transferring the plantlets to a nursery to provide young clone plants of *Quillaja* with a desired saponin profile, for example, X or Some embodiments provide methods for selecting and propagating plants of *Quillaja saponaria* Molina of a defined saponin chemotype comprising the steps of: selecting parental trees by chromatographic analysis of aqueous extracts of sampled plant biomass, for example bark and/or branches and/or twigs, sampling of axillary buds from selected parental trees of defined chemotype, inducing in vitro the shoots of sampled axillary buds, growing in vitro the apical meristems of induced shoots for obtaining plantlets, and transferring the plantlets to small soil containers in a nursery for obtaining clone plants of *Quillaja saponaria* Molina.

Selection of *Quillaja* sp.

In some embodiments the selection of *Quillaja* trees comprises sampling *Quillaja* plant biomass, conducting an aqueous extraction of the plant biomass, analyzing the aqueous extracts of the sampled plant biomass by reverse phase HPLC or UHPLC chromatography, and selecting trees of a defined chemotype, X or R.

In some embodiments, the selection of *Quillaja* trees was performed by sampling of *Quillaja* twigs, analyzing aqueous extracts of the sampled twigs by reverse phase HPLC or UHPLC chromatography, and selecting trees of suitable chemotype.

In some embodiments, determining the chemotype comprises extracting a sample of biomass, injecting the sample into an HPLC (or UPLC) using a flow rate of less than 1 to about 2 mL per minute with water/acetonitrile gradient of about 30% to about 50% acetonitrile, and including about 0.1% to about 0.5% of an acid. In some embodiments, saponins are detected by measurement of the absorbance at 210 nm.

In some embodiments, the acid is an organic acid or a mineral acid. In some embodiments, the acid is selected from formic acid, acetic acid, trifluoroacetic acid, phosphoric acid, citric acid, propionic acid, carbonic acid, and hydrochloric acid.

In some embodiments the selection of *Quillaja* trees was performed by sampling of plant biomass of specimens of *Quillaja saponaria* Molina, analyzing aqueous extracts of the sampled plant biomass by reverse phase HPLC or UHPLC chromatography, and selecting trees of suitable chemotype, for example, the X chemotype, or R chemotype, or for particular saponin ratios, such as QS-21 to QS-17. In some embodiments, selection comprises determining the total saponin content of the biomass.

In some embodiments the selection of *Quillaja* trees was performed by sampling of bark of specimens of *Quillaja saponaria* Molina, analyzing aqueous extracts of the sampled bark by reverse phase HPLC or UHPLC chromatography, and selecting trees of chemotype X. In some embodiments the selection of *Quillaja* trees was performed by sampling of bark of specimens of *Quillaja saponaria* Molina, analyzing aqueous extracts of the sampled bark by reverse phase HPLC or UHPLC chromatography, and selecting trees of chemotype R.

in some embodiments the selection of *Quillaja* trees was performed by sampling of bark of specimens of *Quillaja saponaria* Molina, analyzing aqueous extracts of the sampled bark by reverse phase HPLC or UHPLC chromatography, and selecting trees having a particular QS-21 to QS-17 ratio. In some embodiments the selection of *Quillaja* trees was performed by sampling of bark of specimens of *Quillaja saponaria* Molina, analyzing aqueous extracts of the sampled bark by reverse phase HPLC or UHPLC chromatography, and selecting trees having a particular QS-21 to Rha-QS-17 ratio. In some embodiments the selection comprises determining the total saponin content of the plant biomass.

*Quillaja* Saponin Profile

It was found that the biomass of *Quillaja* plants grown during 1-4 years on an ultrahigh density plantation (surface density, 20,000-100,000 plants/Ha) supplied with irrigation and fertilizers, has an average saponin content on a dry biomass basis ranging between 7-9% for leaf biomass and 3-6% for twig biomass. Likewise, twigs of 3-6 years old *Quillaja* clone trees of chemotype X grown in an ultrahigh-density plantation (surface density, 20,000-100,000 plants/hectare) have a saponin profile enriched in QS-18 and QS-21, and depleted of QS-17. It was found that the saponin profile of the extracts prepared from twig biomass from cultivated clones of chemotype X was superior to bark extracts currently employed for the production of adjuvant-grade saponins of *Quillaja* sp.

in some embodiments, the QS-21 to QS-17 ratio is about 1:1, about 2:1, about 3:1, about 4:1, about 5:1, about 10:1, about 20:1, about 30:1, about 40:1, about 50:1, about 60:1, about 70:1, about 80:1, about 90:1, about 100:1, about 150:1, about 200:1, about 250:1, about 300:1, about 400:1, or about 500:1.

In some embodiments, the QS-21 to Rha-QS-21 ratio is about 1:1, about 2:1, about 3:1, about 4:1, about 5:1, about 10:1, about 20:1, about 30:1, about 40:1, about 50:1, about 60:1, about 70:1, about 80:1, about 90:1, about 100:1, about 150:1, about 200:1, about 250:1, about 300:1, about 400:1, or about 500:1.

In some embodiments, the QS-21 is about 5% of the total saponin content, about 10% of the total saponin content, about 15% of the total saponin content, about 20% of the total saponin content, about 25% of the total saponin content, about 30% of the total saponin content, about 35% of the total saponin content, about 40% of the total saponin content, about 45% of the total saponin content, or about 50% of the total saponin content, about.

In some embodiments, Rha-QS-21 is less than about 50% of the total saponin content, about 45% of the total saponin content, about 40% of the total saponin content, about 35% of the total saponin content, about 30% of the total saponin content, about 25% of the total saponin content, about 20% of the total saponin content, about 15% of the total saponin content, about 10% of the total saponin content, about 8% of the total saponin content, about 6% of the total saponin content, about 4% of the total saponin content. about 2% of the total saponin content, or about 1% of the total saponin content.

In some embodiments, QS-17 is less than about 50% of the total saponin content, about 45% of the total saponin content, about 40% of the total saponin content, about 35% of the total saponin content, about 30% of the total saponin content, about 25% of the total saponin content, about 20% of the total saponin content, about 15% of the total saponin content, about 10% of the total saponin content, about 8% of the total saponin content, about 6% of the total saponin content, about 4% of the total saponin content, about 2% of the total saponin content, or about 1% of the total saponin content.

Some embodiments provide a method for the production of plant material of *Quillaja saponaria* Molina suitable for the extraction and purification of saponins, comprising steps of planting young plants of *Quillaja* trees previously cloned and propagated in a nursery from selected trees, the cultivation of the resulting *Quillaja* plants and harvesting of the cultivated biomass, It was found that of twigs of 3-6 years old *Quillaja* clone trees of chemotype X grown in an ultrahigh-density plantation (surface density, 20,000-100,000 plants/hectare) have a saponin composition enriched in QS-18 and QS-21, and depleted of QS-17, relative to non-plantation *Quillaja* trees. Similarly, the saponin composition of the extracts prepared from twig biomass from cultivated clones of chemotype X was superior to bark extracts employed currently for the production of adjuvant-grade saponins of *Quillaja saponaria* Molina. In particular, the cultivated clones provide lower amounts of QS-17 and R-series saponins.

Some embodiments provide R-series saponin compositions. It was found that of twigs of 3-6 years old *Quillaja* clone trees of chemotype R grown in an ultrahigh-density plantation have a saponin composition enriched in Rha-QS-18 and Rha-QS-21, and depleted of Rha-QS-17, relative to pooled fractions from non-plantation *Quillaja* trees. Likewise, the extract prepared from twig biomass from cultivated clones of chemotype R was a new source for the purification and isolation of Rha-QS-18 and Rha-QS 21.

Propagating *Quillaja* sp. Clones

In some embodiments, axillary buds sampled from selected *Quillaja* trees are induced in vitro to provide induced shoots. In some embodiments, explants of the apical meristems of the induced shoots are transferred to sterile media for vegetative propagation of clone seedlings. In some embodiments, the clone seedlings are grown in nurseries to obtain young *Quillaja* plants.

*Quillaja* Plantations

In some embodiments, harvesting comprises removing plant bark, removing plant aerial biomass, removing plant leaves, removing plant twigs, removing plant branches, and/or combination of the foregoing.

In some embodiments the harvesting is performed after three years of growth in the ultrahigh-density plantation. In some embodiments the remaining stumps are allowed to re-grow during three years and harvested cyclically every three years onwards. In some embodiments 25 Ton of dry aerial biomass are harvested per hectare of ultrahigh density plantation after three years of growth.

In some embodiments the ultrahigh-density plantation contains predominantly *Quillaja* plants of chemotype X. In some embodiments the ultrahigh-density plantation contains predominantly *Quillaja* plants of chemotype X/R. In some embodiments the ultrahigh-density plantation contains predominantly *Quillaja* plants of chemotype R. For example, in some embodiments, the majority of the plants in the plantation are of chemotype X.

In some embodiments the *Quillaja* biomass is harvested after about one year, after about two years, after about three years, after about four years, after about five years, after about six years, after about seven years, after about eight years, after about nine years, or after about ten years.

In some embodiments, harvesting comprises removing plant bark, removing plant aerial biomass, removing plant leaves, removing plant twigs, removing plant branches, and/or combination of the foregoing. In some embodiments, harvesting comprises removing the entire plant.

In some embodiments, the biomass is harvested after 2 years of growth at a density of about 60,000 plants/hectare. In some embodiments, the biomass is harvested after 3 years of growth at a density of about 60,000 plants/hectare. In some embodiments, the biomass is harvested after 2 years of growth at a density of about 50,000 plants/hectare. In some embodiments, the biomass is harvested after 3 years of growth at a density of about 50,000 plants/hectare. In some embodiments, the biomass is harvested after 2 years of growth at a density of about 40,000 plants/hectare, In some embodiments, the biomass is harvested after 3 years of growth at a density of about 40,000 plants/hectare.

Some embodiments provide methods of cultivating ultra-high-density plantations of cloned *Quillaja* plants. In some embodiments, plants of a single clone are planted at ultra-high-density, for example, from about 20,000 to about 100,000 plants per hectare. In some embodiments, plants of a single clone are planted at about 30,000 to about 100,000 plants per hectare. In some embodiments, plants of a single clone are planted at about 40,000 to about 100,000 plants per hectare. In some embodiments, plants of a single clone are planted at about 50,000 to about 100,000 plants per hectare. In some embodiments, plants of a single clone are planted at about 60,000 to about 100,000 plants per hectare, In some embodiments, plants of a single clone are planted at about 70,000 to about 100,000 plants per hectare. In some embodiments, plants of a single clone are planted at about 90,000 to about 100,000 plants per hectare. In some embodiments, plants of a single clone are planted at about 100,000 to about 100,000 plants per hectare. In some embodiments, the plantation comprises *Quillaja* trees cloned from a single tree.

Some embodiments provide methods of cultivating high-density plantations of cloned *Quillaja* plants, In some embodiments, plants of a single clone are planted at high-density, for example, from about 2,000 to about 20,000 plants per hectare. In some embodiments, plants of a single clone are planted at about 3,000 to about 20,000 plants per hectare. In some embodiments, plants of a single clone are planted at about 4,000 to about 20,000 plants per hectare. In some embodiments, plants of a single clone are planted at about 5,000 to about 20,000 plants per hectare. In some embodiments, plants of a single clone are planted at about 6,000 to about 20,000 plants per hectare. In some embodiments, plants of a single clone are planted at about 7,000 to about 20,000 plants per hectare. In some embodiments, plants of a single clone are planted at about 8,000 to about 20,000 plants per hectare. In some embodiments, plants of a single clone are planted at about 9,000 to about 20,000 plants per hectare. In some embodiments, plants of a single clone are planted at about 10,000 to about 20,000 plants per hectare. In some embodiments, plants of a single clone are planted at about 11,000 to about 20,000 plants per hectare. In some embodiments, plants of a single clone are planted at about 12,000 to about 20,000 plants per hectare. In some embodiments, plants of a single clone are planted at about 13,000 to about 20,000 plants per hectare. In some embodiments, plants of a single clone are planted at about 14,000 to about 20,000 plants per hectare. In some embodiments, plants of a single clone are planted at about 15,000 to about 20,000 plants per hectare. In some embodiments, plants of a single clone are planted at about 16,000 to about 20,000 plants per hectare. In some embodiments, plants of a single clone are planted at about 17,000 to about 20,000 plants per hectare. In some embodiments, plants of a single clone are planted at about 18,000 to about 20,000 plants per hectare. In some embodiments, plants of a single clone are planted at about 19,000 to about 20,000 plants per hectare. In some embodiments, the plantation comprises *Quillaja* trees cloned from a single tree.

Some embodiments provide methods of cultivating medium-density plantations of cloned *Quillaja* plants. In some embodiments, plants of a single clone are planted at medium-density, for example, from about 500 to about 2,000 plants per hectare. In some embodiments, plants of a single clone are planted at about 750 to about 2,000 plants per hectare. In some embodiments, plants of a single clone are planted at about 1,000 to about 2,000 plants per hectare. In some embodiments, plants of a single clone are planted at about 1,250 to about 2,000 plants per hectare. In some embodiments, plants of a single clone are planted at about 1,500 to about 2,000 plants per hectare. In some embodiments, plants of a single clone are planted at about 1,750 to about 2,000 plants per hectare. In some embodiments, the plantation comprises *Quillaja* trees cloned from a single tree.

Some embodiments provide methods of cultivating low-density plantations of cloned *Quillaja* plants. In some embodiments, plants of a single clone are planted at low-density, for example, from about 1 to about 500 plants per hectare. In some embodiments, plants of a single clone are planted at about 100 to about 500 plants per hectare. In some embodiments, plants of a single clone are planted at about 200 to about 500 plants per hectare. In some embodiments, plants of a single clone are planted at about 300 to about 500 plants per hectare. In some embodiments, plants of a single clone are planted at about 400 to about 500 plants per hectare. In some embodiments, the plantation comprises *Quillaja* trees cloned from a single tree.

Some embodiments further comprising contacting the plantations with fertilizer comprising at least about 150 kg of nitrogen per hectare. In some embodiments the fertilizer comprises at least about 150 kg of nitrogen and about 100 kg of phosphorus per hectare. In some embodiments the fertilizer comprises at least about 150 kg of nitrogen, about 100 kg of phosphorus, and at least 150 kg of potassium per hectare. In some embodiments the fertilizer comprises between 150-250 kg of nitrogen, between 90-100 kg of phosphorus, and between about 150-250 kg of potassium per hectare. In some embodiments the fertilizer comprises at least about 200 kg of nitrogen, about 100 kg of phosphorus, and about 200 kg of potassium per hectare. In some embodiments the fertilizer comprises between 150-250 kg of nitrogen, between 90-100 kg of phosphorus, and between about 150-250 kg of potassium per hectare, Additional embodiments are disclosed in further detail in the following examples, which are not in any way intended to limit the scope of the claims.

EXAMPLES

Example 1

Selection of *Quillaja* Trees

Samples of bark were taken from 33 specimens of *Quillaja saponaria* Molina grown in forests in Chile. The samples were dried, milled and extracted with water at 60° C. for 3 hours (mass ration bark/water=1:15) in a temperature-controlled water-bath with continuous shaking. An aliquot of the resultant extract was filtered and analyzed by reverse phase HPLC to determine the chemotype of the sampled specimens.

Figure 11A:
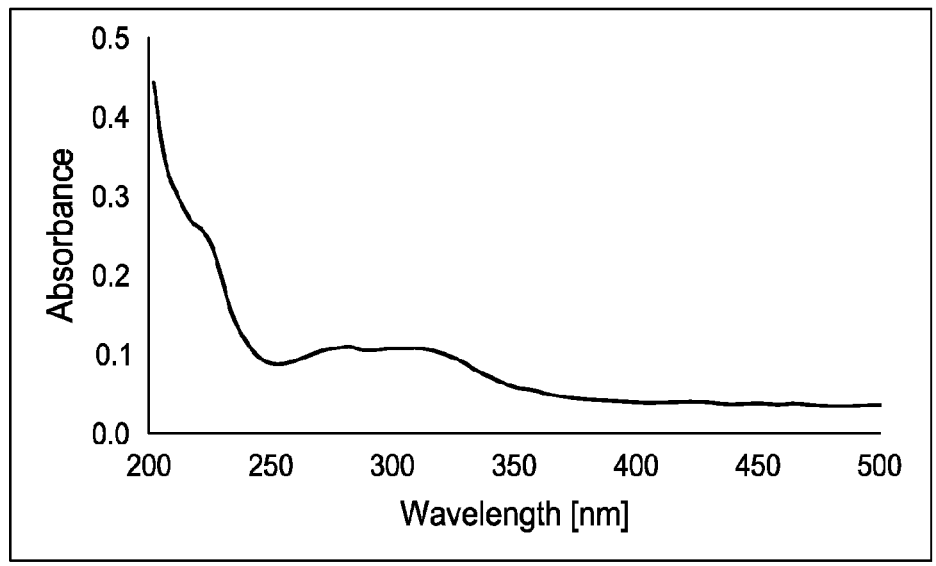
FIG. 11 depicts representative absorbance spectra of extracted *Quillaja* biomass from a high-density plantation (FIG. 11A) relative to pooled fractions of bark from wild *Quillaja* trees (FIG. 11B).
Figure 11B:
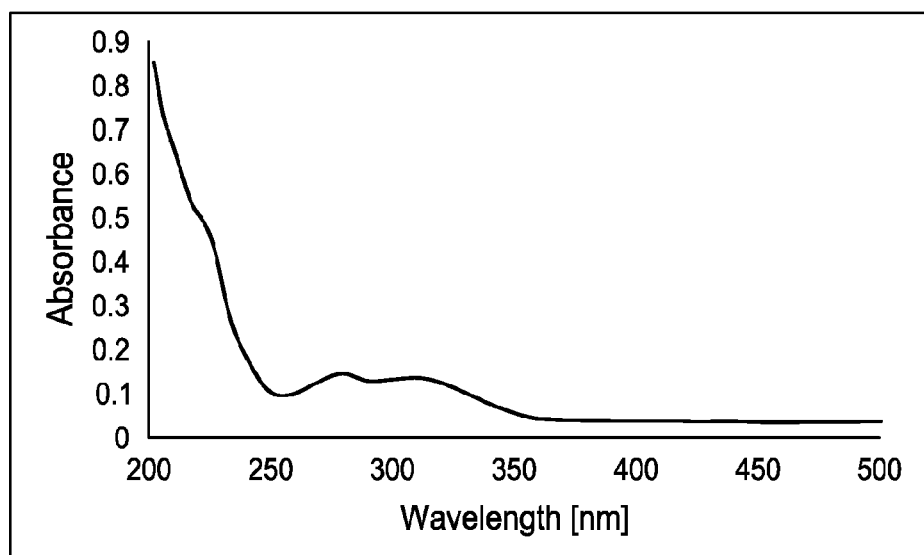

Chemotype was determined by injecting an extract sample into a C4 column (particle size, 5 µm; inner diameter, 4.6 mm; length, 25 cm) at 30° C., with a flow rate of 1.0 ml/min in a water/acetonitrile gradient (30% to 45% acetonitrile) with 0.15% trifluoroacetic acid. Saponins were detected using absorbance at 210 nm. A representative absorbance spectrum is depicted in FIG. 11.

Figure 4A:
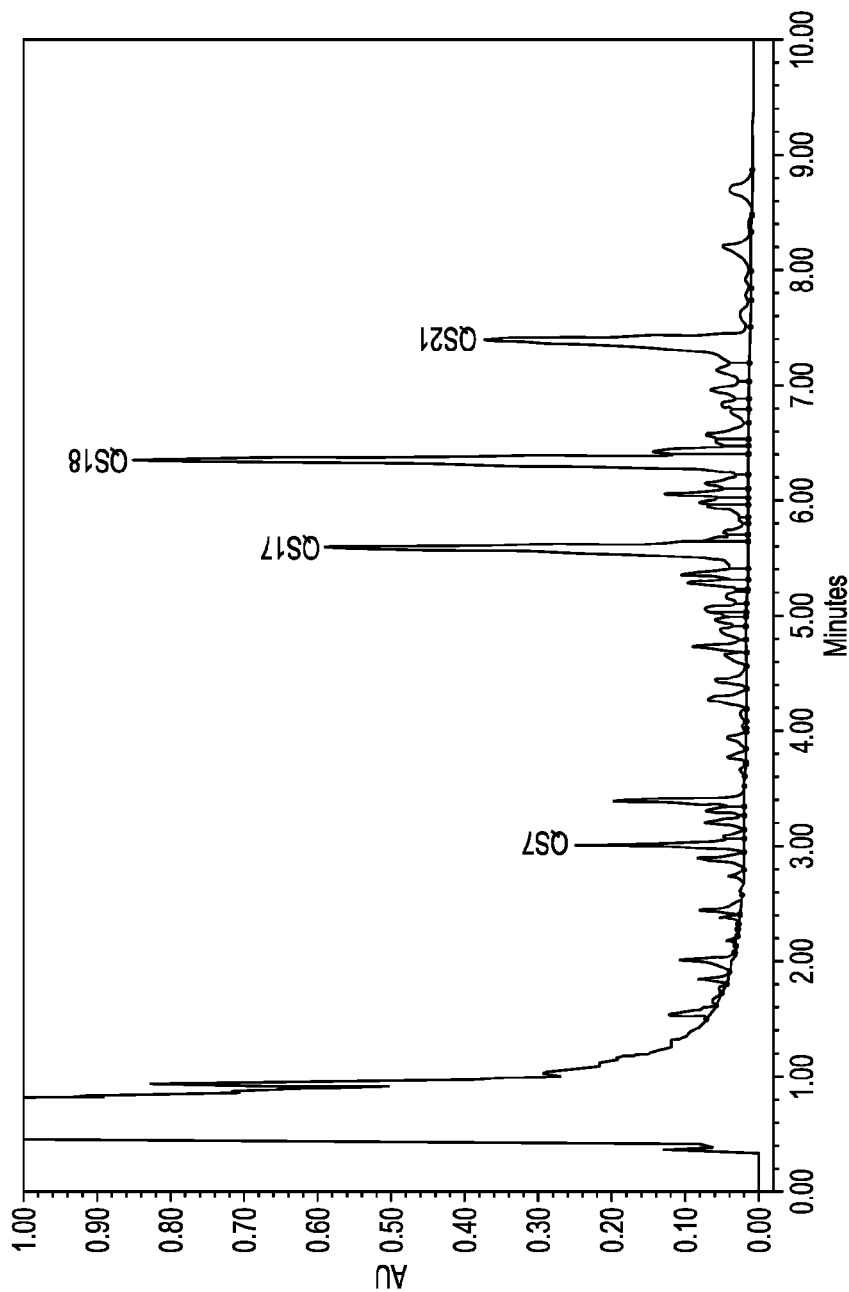
FIG. 4 depicts representative HPLC chromatograms of the extracts of bark samples for the: X (FIG. 4A), X/Y (FIGS. 4B and 4C) and R (FIG. 4D) chemotypes of *Quillaja saponaria* Molina.
Figure 4B:
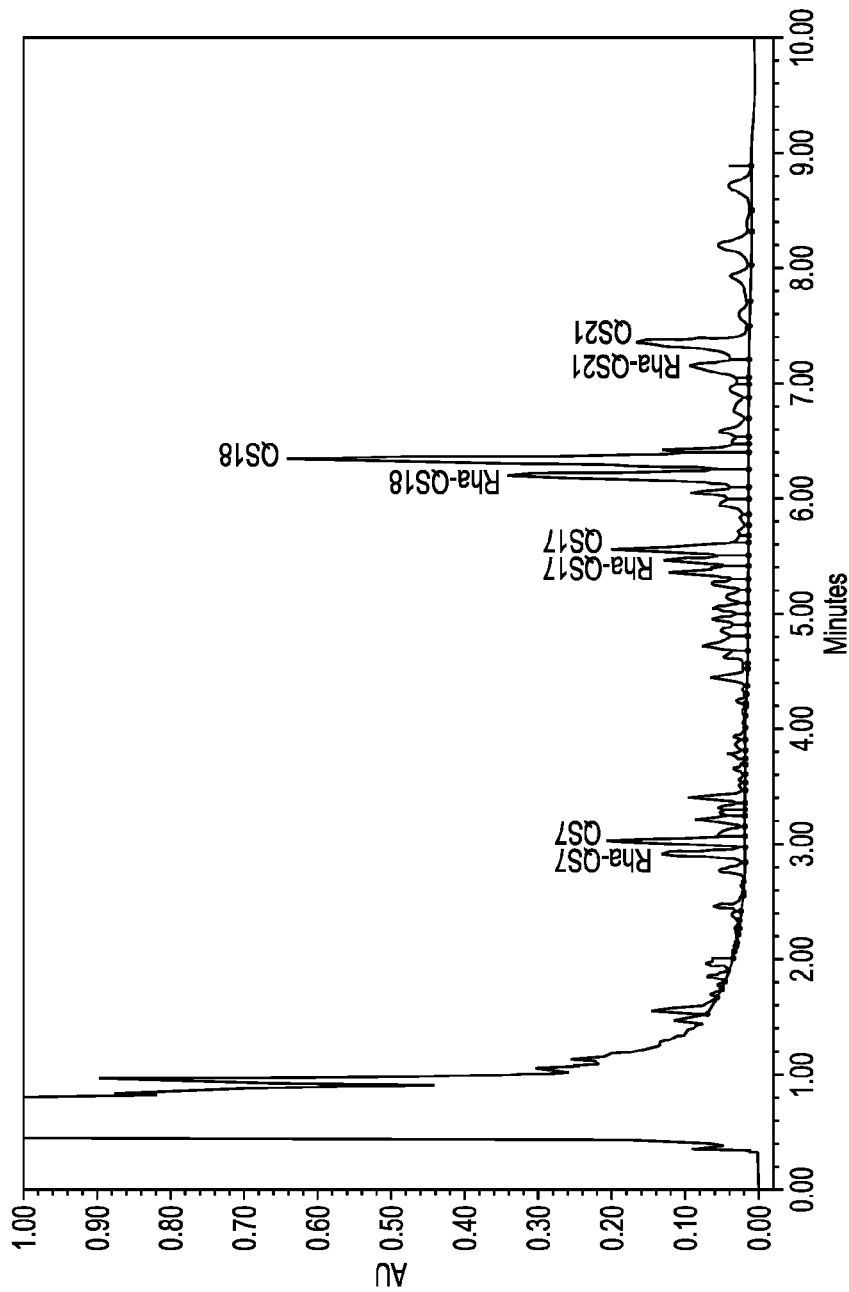
Figure 4C:
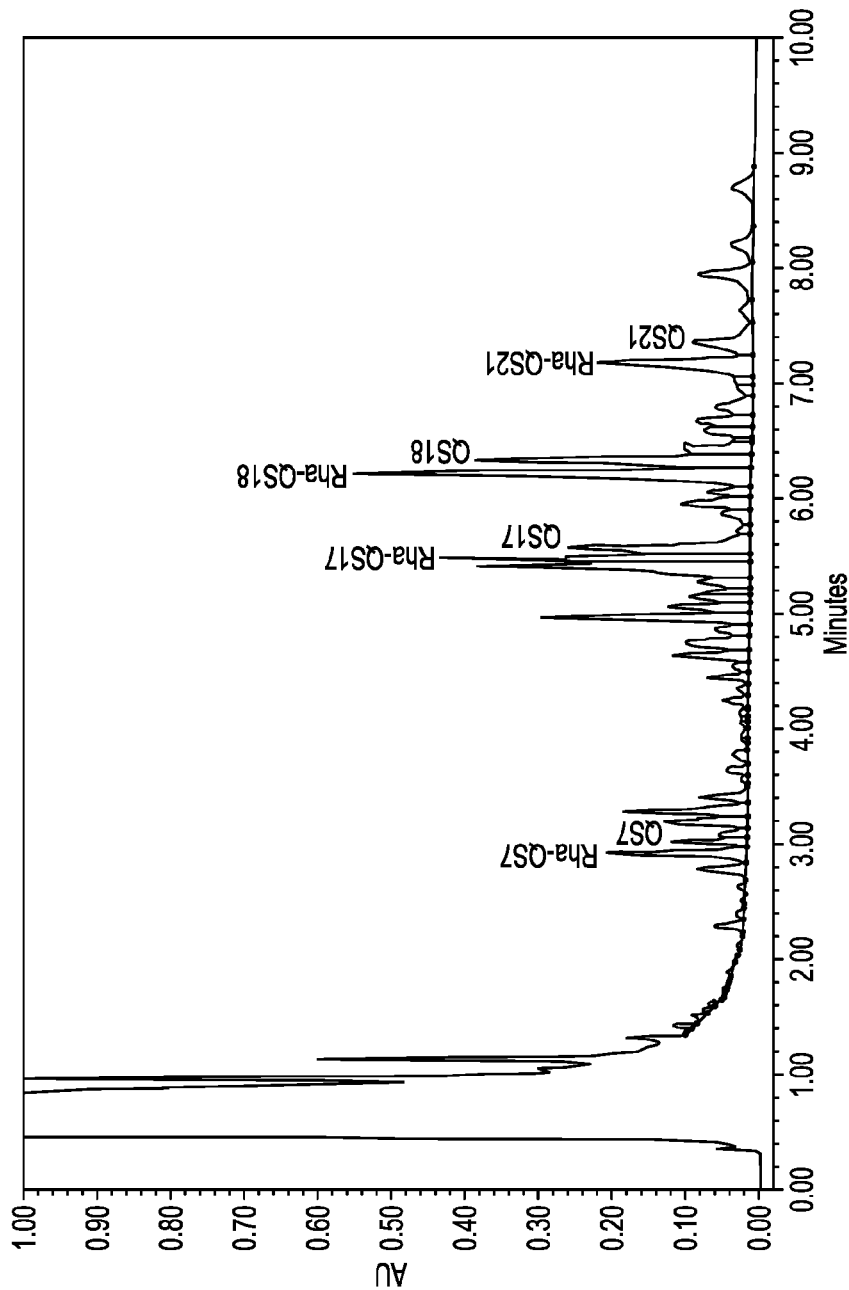
Figure 4D:
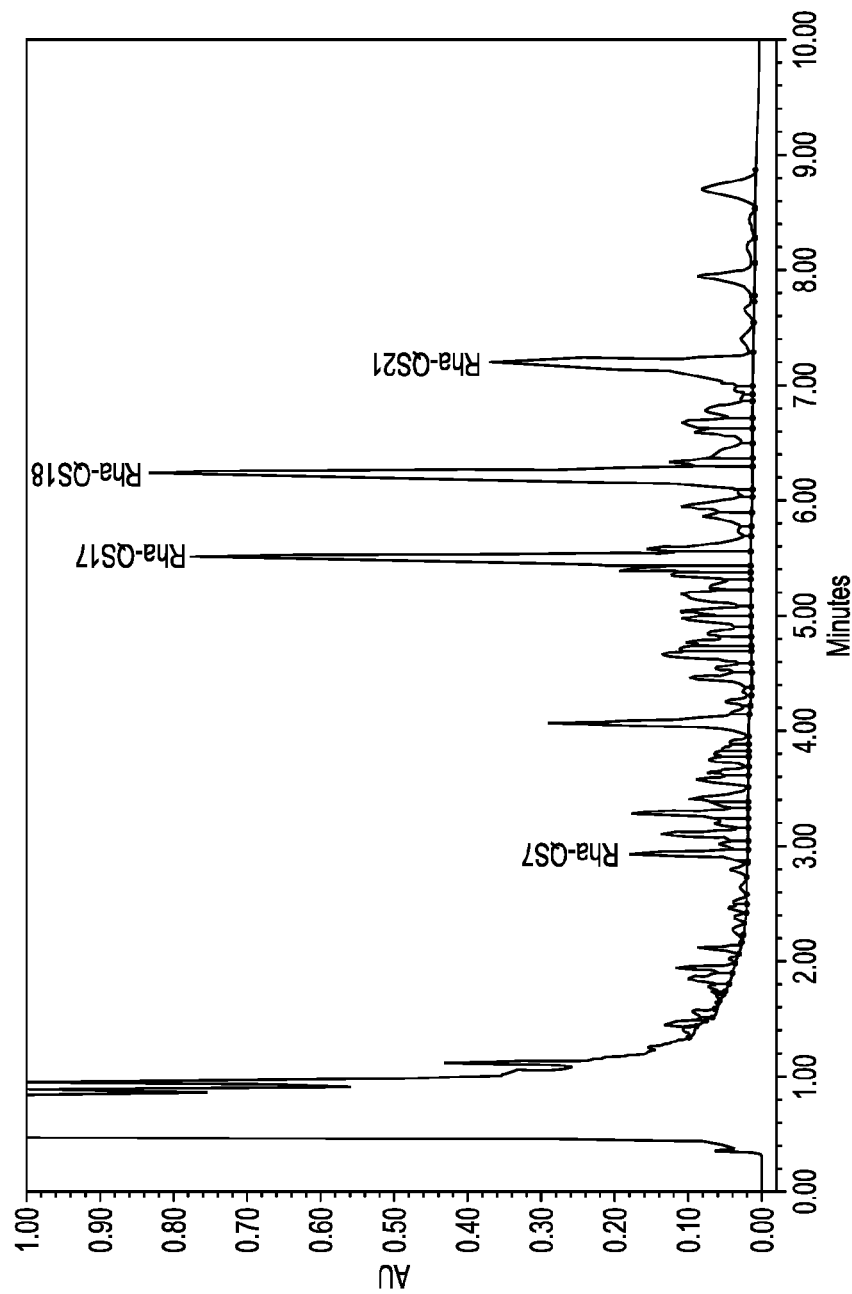

Three chemotypes of *Quillaja* trees were identified: i) Chemotype X: containing saponins belonging to the X-series, substantially free of saponins belonging to the R-series; ii) Chemotype X/Y: containing saponins belonging to X- and R-series, and; iii) Chemotype R: containing saponins belonging to the R-series, substantially free of saponins belonging to the X-series. Table 1 summarizes the results obtained and FIG. 4 provides examples of HPLC profiles of each chemotype identified: X (FIG. 4A), X/Y (FIGS. 4B and 4C) and R (FIG. 4D).

TABLE 1

Chemotypes of non-plantation *Quillaja* Trees

| Chemotype | Quantity of Trees | Percent |
|---|---|---|
| X | 11 | 33.3 |
| X/R | 17 | 51.5 |
| R | 5 | 15.2 |
| TOTAL | 13 | 100 |

Example 2

Cloning of Selected *Quillaja* Trees

Trees belonging to all three chemotypes (X, R, and X/R) were used as sources of shoots. Branches of selected trees were sprayed with a mixture of Captan and Benlate (1.8 g/l). After the second spraying Benlate, samples of twigs with fresh shoots were collected and explants of axillary buds were taken and cultivated ill vitro as sources of new shoots. The cultivation was performed in sterile glass flasks containing medium MS at pH 5.7, supplemented with sucrose (2%), agar (0.8%), vitamins and indolebutyric acid (IBA) (0.6 mg/l) to induce growth of new buds. The flasks were incubated at 23 ° C. with 14 hours light regime of 40 µmol-2s-1 provided by daylight.

Figure 5:
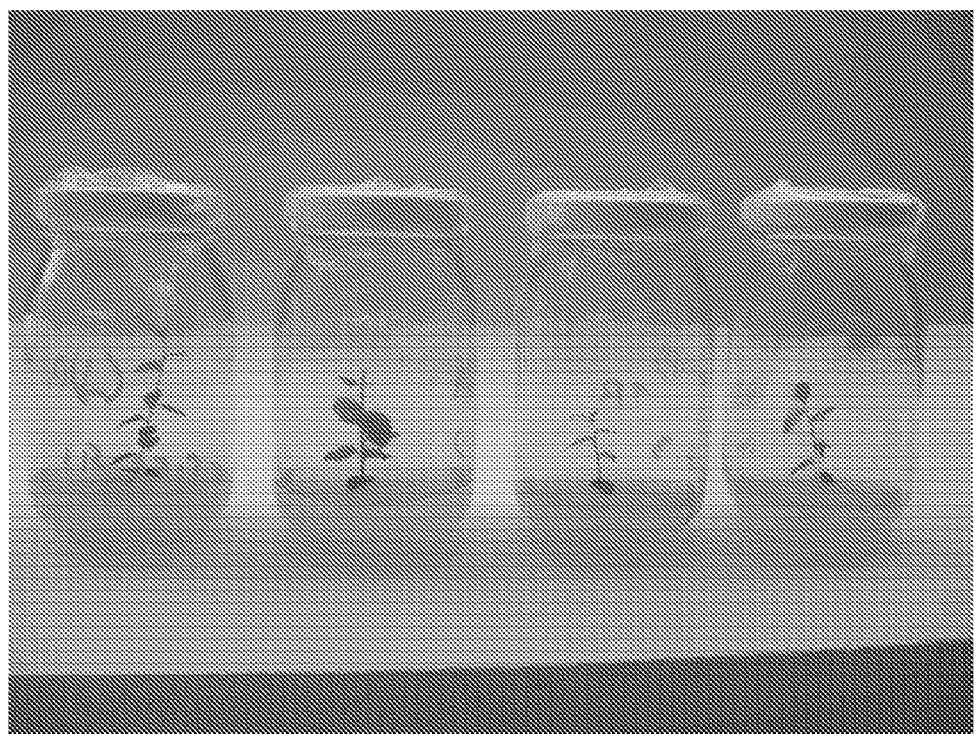
FIG. 5 depicts cloned plantlets of *Quillaja saponaria* Molina obtained by propagation of explants of apical shoot meristems taken from axillary buds.
Figure 6:
FIG. 6 depicts a young clone plant of *Quillaja saponaria* Molina growing in plastic containers filled with coconut fiber to facilitate plant growth and complete root development.

After 2 months, explants of new buds were subcultured in the same culture medium, the explants of new buds became plantlets (FIG. 5). The plantlets (3 a 5 cm) were then transferred to containers (200 ml) filled with peat (50%) and coconut fiber (50%), to continue growing in a nursery and to promote the development of roots. After six months in the nursery (FIG. 6), the plants obtained were transferred to an outdoor plantation.

Example 3

Cultivation of *Quillaja* Trees in High-Density Plantations

Young *Quillaja* plants produced by vegetative propagation as described in Example 2. were planted in outdoor plots divided in rows (1.2 m wide). Rows were uniformly spaced by 0.6 m. Cloned plants were manually transferred and planted in the rows. The plant density in each plot was in the range of 20,000-100,000 plants/hectare. The plot was irrigated at a maximum irrigation rate of 61 m$^3$/ha/hour through two parallel irrigation lines installed in each row of the plot. Fertilizers were supplied through the irrigation lines to the plots; the dosage of fertilizers was as follows: 180 kg N/ha/year, 120 kg N/ha/year, and 100 kg K$_2$O/ha/year. Weed control was performed by manual procedures. The plot was subdivided in three independent pads as described in Table 2.

TABLE 2

Plant distribution in the outdoor plot described in Example 3.

| Clone | Chemotype | Clone Qty in Pad 1 | Clone Qty in Pad 2 | Clone Qty in Pad 3 |
|---|---|---|---|---|
| B | R | 75 | — | — |
| E | X | 47 | — | — |
| V | X/R | 13 | — | 68 |
| AB | X | 36 | — | 28 |

TABLE 2-continued

Plant distribution in the outdoor plot described in Example 3.

| Clone | Chemotype | Clone Qty in Pad 1 | Clone Qty in Pad 2 | Clone Qty in Pad 3 |
|---|---|---|---|---|
| K | X | 19 | — | — |
| AK | X | 3 | 89 | — |
| J | X | — | 14 | 45 |
| W | X/R | — | — | 58 |
| G | X | — | — | 44 |
| A | X | — | — | 61 |

Figure 7A:
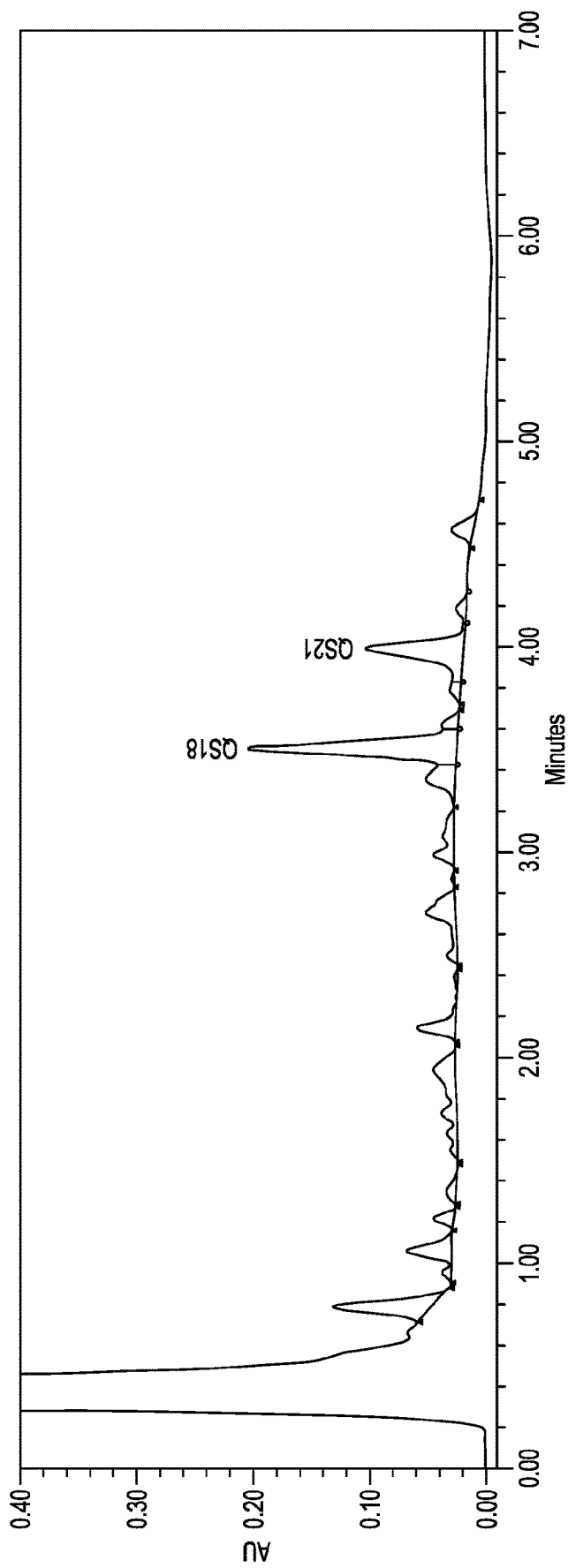
FIG. 7 depicts the reverse phase UHPLC chromatograms of sample extracts of twigs of a representative cloned *Quillaja saponaria* Molina of the chemotype X after 10 months in an ultra-high density plantation (7A); an extract of a pool of *Quillaja* bark collected in the wild forest (7B) and; an extract of a pool of *Quillaja* whole wood collected in the wild forest (7C).
Figure 7B:
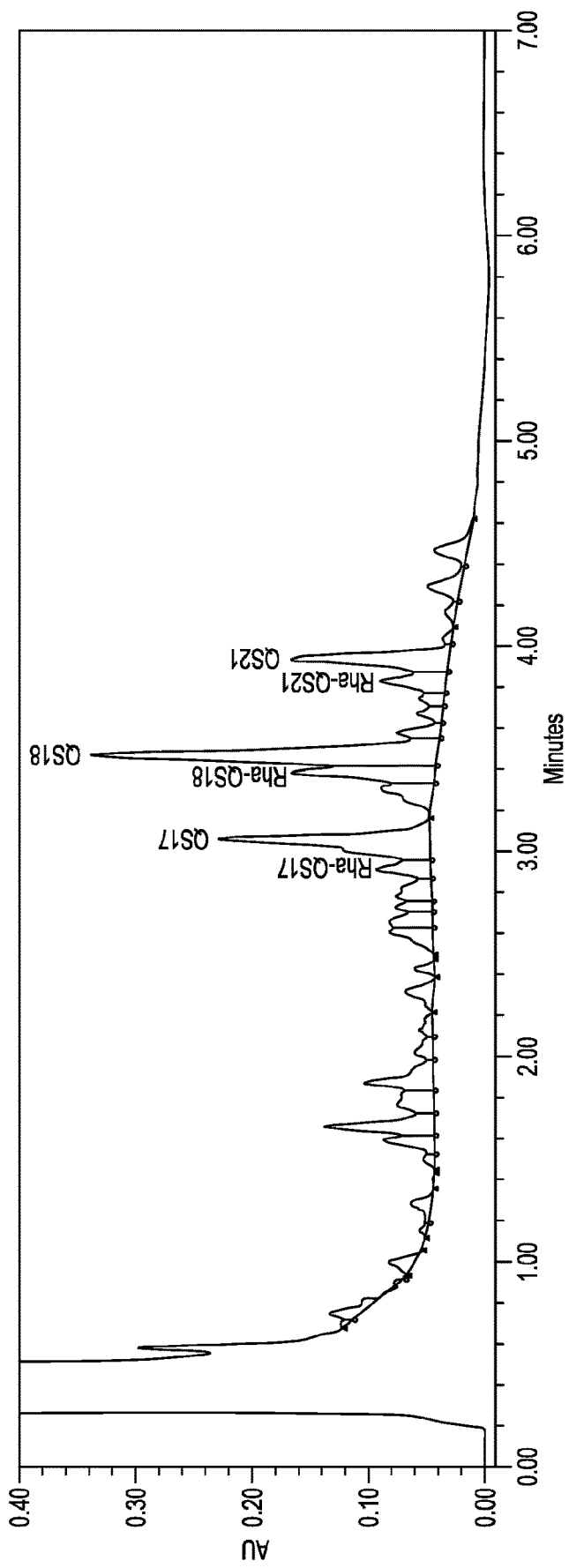
Figure 7C:
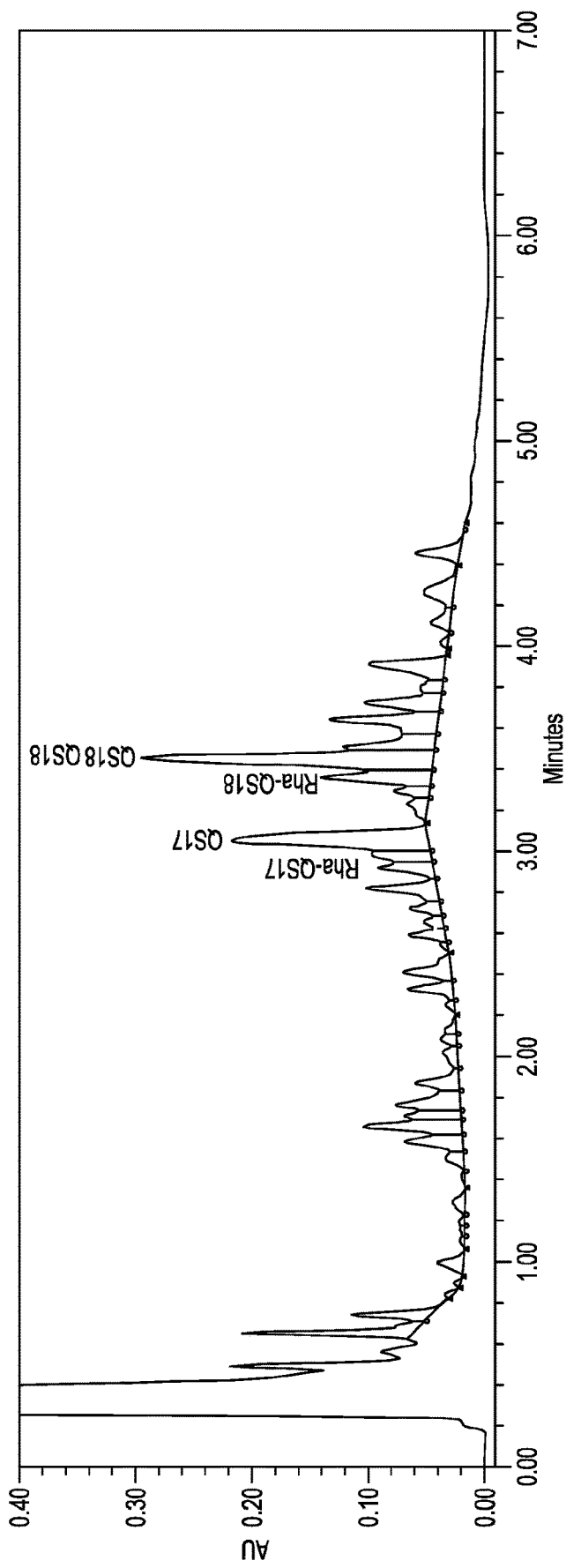
Figure 8A:
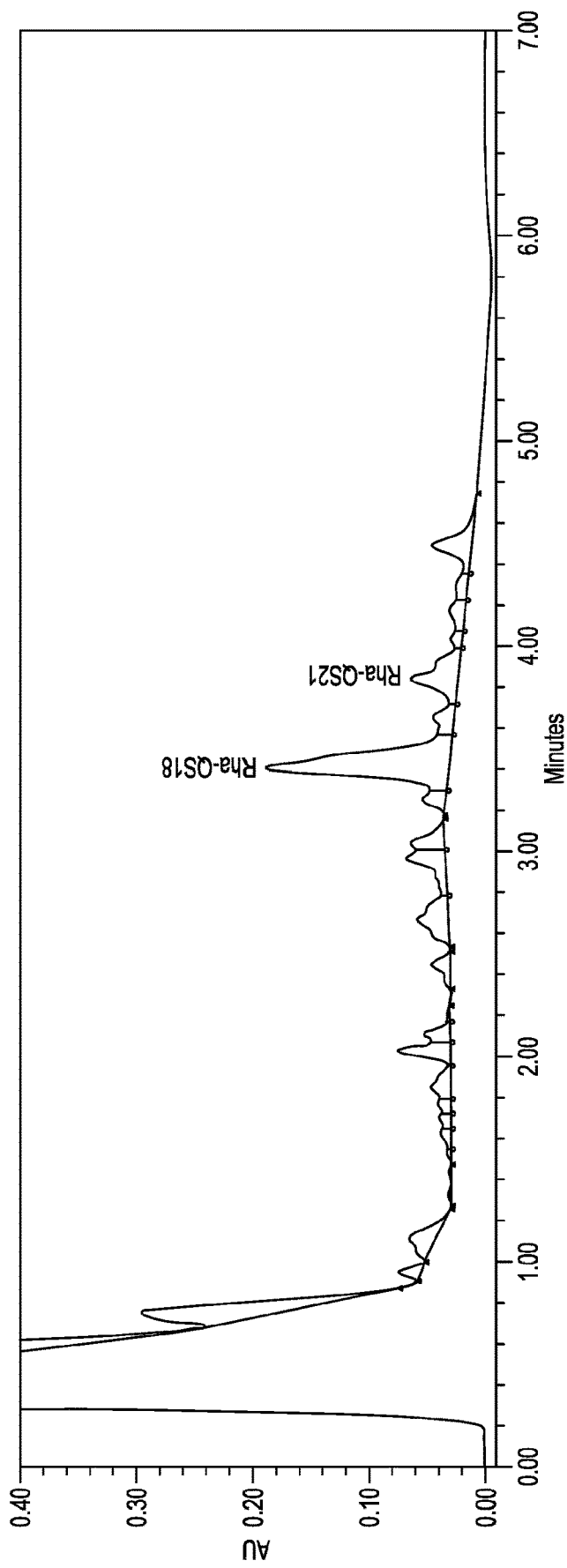
FIG. 8 depicts the reverse phase UHPLC chromatograms of sample extracts of twigs and leaves of a representative cloned *Quillaja saponaria* Molina of the chemotype R after 10 months in an ultra-high density plantation (8A); an extract of a pool of *Quillaja* bark collected in the wild forest (8B) and; an extract of a pool of *Quillaja* whole wood collected in the wild forest (8C).
Figure 8B:
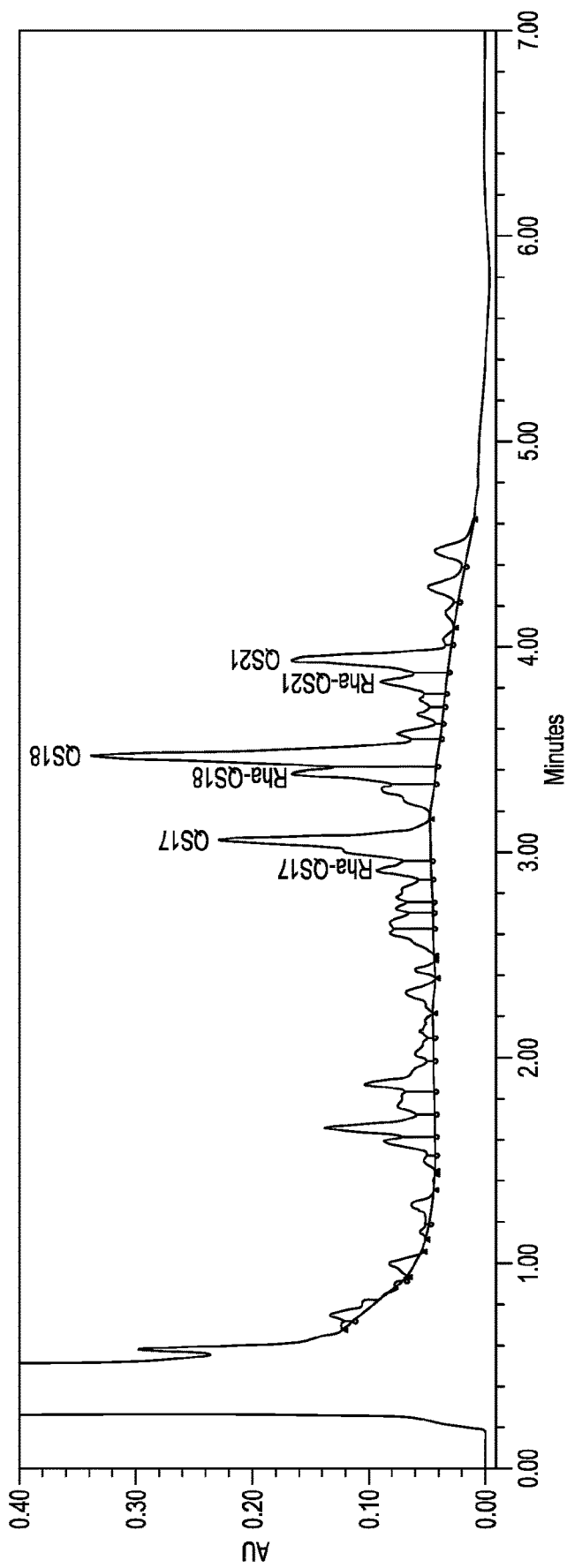
Figure 8C:
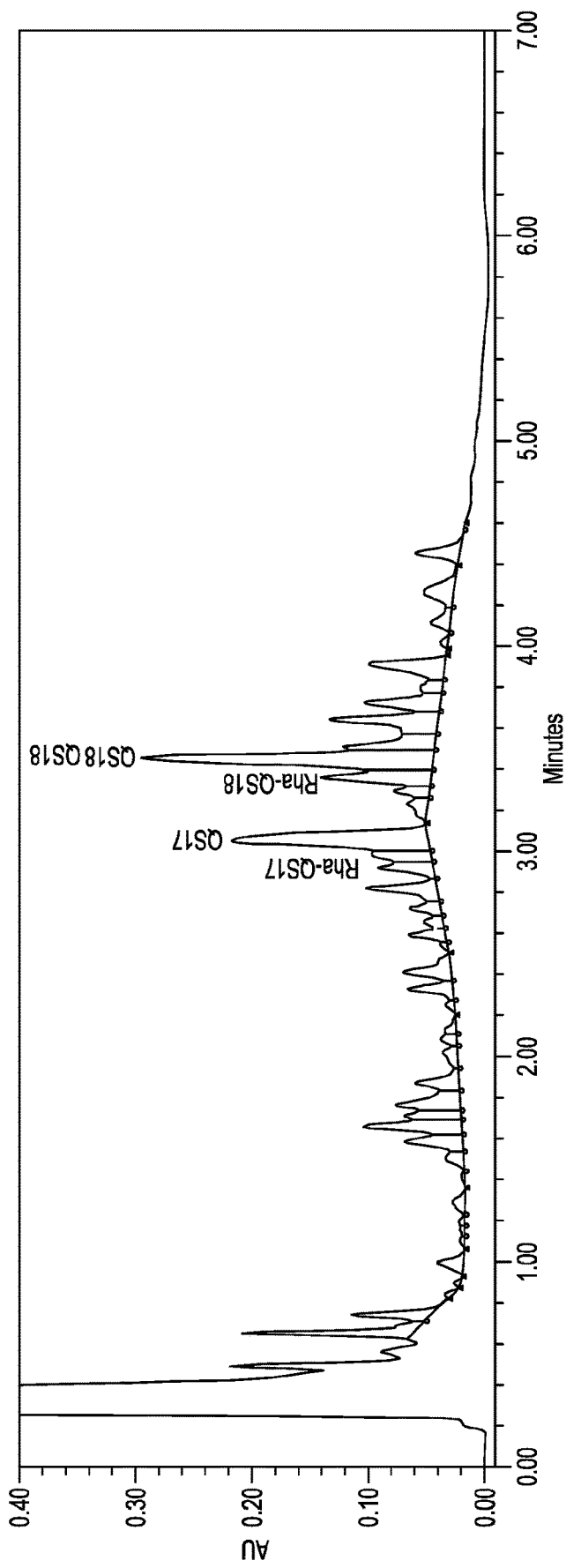

After 10 months of growth, samples of twigs and leaves were taken from clone plants and their saponin profile was determined by reverse phase UHPLC. The samples were dried, milled and extracted with water at 60° C. for 3 hours (mass ration bark/water=1:15) in a temperature-controlled water-bath with continuous shaking. An aliquot of the resultant extract was filtered and analyzed by reverse phase UHPLC to determine the saponin profile of the sampled specimens. An aliquot of each extract was injected into a C18 column (particle size 1.7 μm, inner diameter 2.1 mm; length 50 mm) at 30° C., with a flow rate of 0.41 ml/min in a water/acetonitrile gradient (34% to 45% acetonitrile) with 0.15% formic acid. Saponins were detected using absorbance at 210 nm. The saponin profiles of the clone plants were advantageous relative to extracts of either bark or pruned biomass from non-plantation trees, as determined by UHPLC analysis of samples twigs of the cultivated clone plants (FIGS. 7 and 8).

Compared to the bark extract of the parent tree, the saponin profile of the twigs from clone plants of chemotype X grown in the high density plantation was less heterogeneous, with strong predominance of QS-18 and QS-21 and substantially free of QS-17 and saponins of the R-series. Likewise, when compared to the bark extract of the parental tree, the saponin profile of the twigs from clone plants of the chemotype R grown in the high density plantation was also less heterogeneous, with strong predominance of Rha-QS-18 and Rha-QS-21 and substantially free of Rha-QS-17 and saponins of the X-series. Therefore, the twigs of young biomass harvested from high-density plantations of *Quillaja* plants of defined chemotype are a suitable for further production of extracts of saponins or saponin-like compounds on large scale.

Example 4

Harvesting Extraction and Purification of the Biomass Cultivated in Plantations

A outdoor plot, similar to Example 3, is planted with clone plants of a single chemotype (20,000-100,000 plants/hectare) and cultivated for three years according to the conditions described above in Example 3.

Figures 9A, 9B:
FIG. 9 depicts an ultra-high density plantation of *Quillaja saponaria* Molina after 3 years of growth (FIG. 9A) and after mechanical harvesting of the biomass (FIG. 9B).

The plants are then mechanically harvested to render fresh biomass (FIG. 9). The fresh biomass is dried, chipped, and sieved to remove fine fraction resulting from milled leaves, provided a sample of chipped dried twigs.

The biomass described above, obtained from a plantation of clones belonging to a unique chemotype, is extracted to provide homogenous saponin extracts. 350 kg of chipped dry twigs of *Quillaja saponaria* Molina are extracted with 1150 L of water heated to 60° C. for 3 hours. The resulting plant extract solution contains about 60 g/L of total soluble solids. The plant extract is transferred to a stirred tank and kept at 15° C.

The pH of the cooled plant extract is adjusted to 4.3-4.5 by addition of HCl 20 kg of PVPP and 50 L of an aqueous suspension of bentonite (75 g/L) are added to the acidified plant extract. The suspension is filtered through diatomaceous earth to produce a clarified extract. Water is then removed by nano-filtration to produce a concentrated extract with about 85-100 g extracted solutes/L. Additional water and low molecular weight impurities are removed from the concentrated extract by ultra-filtration (10,000-75,000 Da cutoff). When the solute concentration in the extract reaches between 200-250 g extracted solutes/L, the filtration is changed to diafiltration mode to produce a liquid precursor containing 130-150 g extracted solutes/L. The saponin purity in the liquid precursor is between 86-94% (w/w). The liquid precursor is then pasteurized by heating to 86° C. for 30-120 min to provide the final liquid product. The pasteurized liquid product may be spray-dried at a temperature between 160° C. and 200° C. to produce a powdered extract.

Example 5

Purification of Saponins from Twig Biomass from an Ultrahigh-Density Plantation with X-series and R-series Clone Plants 60 g of purified saponin extract is suspended in 600 ml of methanol. The solids are extracted with stirring at 30° C. for 15 min. Undissolved solids are removed by centrifugation. The methanol extract is concentrated by vacuum evaporation to a final concentration of 180 g solids/L.

Aliquots of the concentrated methanol extract are injected in a semipreparative reverse phase HPLC column (inner diameter 21.2 mm; length 250 mm; particle size 7 pm) and eluted with water/methanol (72:28) with 0.15% formic acid at a flow rate of 20 ml/min. The saponin profile of the collected fractions is then determined by reverse phase UHPLC. Fractions containing the target saponin are selected for further purification. The selected fractions of 10-200 preparative runs are pooled and solvent is removed under vacuum. The residual aqueous solution is lyophilized, rendering the intermediate fraction of the target saponin.

The lyophilized fraction is dissolved in a mixture of water/acetonitrile (70:30). Aliquots of the resulting solution are injected in a semipreparative reverse phase HPLC column (inner diameter 21.2 mm; length 250 mm; particle size 7 μm) and eluted with a solvent gradient of water/methanol (35% to 52% acetonitrile) with 0.15% formic acid at a flow rate of 17 ml/min. The saponin profile of the collected fractions is then determined by reverse phase UHPLC. Fractions containing the target saponin are selected for further purification, the fractions pooled, and the solvent removed under vacuum. The residual aqueous solution is lyophilized, rendering the purified target saponin. This method is used to produce large quantities of QS-21, QS18, Rha-QS-18, and Rha-QS21.

Example 6

Production of Young Plants of *Quillaja saponaria* Molina

Young *Quillaja saponaria* Molina plants were propagated in a nursery for 8-9 months. During the growth in the nursery, the containers were periodically irrigated, and were supplied with 200 ppm nitrogen twice per week until the sixth month of growth. The morphophysiological attributes of the resulting plants are summarized in Table 3.

TABLE 3

Morphology of 8-month-old *Quillaja saponaria* Molina plants in a Nursery

| Height [cm] | Diameter [mm] | Weight [g/plant] | Foliar area [cm$^2$/plant] | Root growth potential [n° of roots/plant] | Hydric potential [Bar] |
|---|---|---|---|---|---|
| 20 | 3.5 | 2.2 | 140 | 24 | 3.0 |

Example 7

Effect of the Plantation Density on Saponin Yields

The young *Quillaja saponaria* Molina plants produced in the Example 7 were planted in outdoor plots to assess the impact of plantation density on biomass and saponin profile over 5 months of growth.

The outdoor plots were divided in rows (1.2 m wide), uniformly spaced by walkways (0.6 m wide). The young plants were manually transplanted into three plantation densities: 22,000; 50,000 and 100,000 plants/hectare (relative to less than 500 plants/hectare in the wild. The plots were periodically irrigated through two parallel irrigation lines installed in each row of the plot. Fertilizers were supplied once at 200 kg N/ha, 100 kg $P_2O_5$/ha, and 200 kg $K_2O$/ha. The morphological attributes of the plants grown 5 months on each density are summarized in Table 4.

TABLE 4

Morphology of 5-month-old *Quillaja* Plants from an Ultrahigh-density Plantation

| Density [plants/hectare] | Height [cm] | Diameter [cm] | Leaf dry mass/plant [g/plant] | Stem and Twig dry mass/plant [g/plant] | Aerial Biomass dry mass/plant [g/plant] |
|---|---|---|---|---|---|
| 22,000 | 52.5 | 8.6 | 18.6 | 13.8 | 37.4 |
| 50,000 | 62.8 | 9.5 | 33.8 | 26.8 | 60.6 |
| 100,000 | 56.5 | 8.2 | 26.3 | 18.5 | 44.8 |

The content of saponins in samples of leaf and twig biomass was determined according to the chromatographic procedure described in the Example 8, The yields of biomass and saponins of the ultrahigh density plantations under study are summarized in Table 5.

TABLE 5

Biomass and Saponin Yields of 5-month-old *Quillaja* Plants from an Ultrahigh-density Plantation

| Plantation density [plants/Ha] | Dry mass (leaves) [Kg/Ha] | Dry mass (stem/twig) [Kg/Ha] | Dry mass (aerial biomass) [Kg/Ha] | Saponins (leaves) [Kg/Ha] | Saponins (stem/twig) [Kg/Ha] | Saponins (aerial biomass) [Kg/Ha] |
|---|---|---|---|---|---|---|
| 22,000 | 412 | 307 | 719 | 35 | 6 | 41 |
| 50,000 | 1,689 | 1,342 | 3,031 | 154 | 58 | 212 |
| 100,000 | 2,633 | 1,852 | 4,485 | 220 | 46 | 266 |

Example 8

Effect of Fertilizer on Saponin Profile

Young *Quillaja saponaria* Molina plants produced as described in Example 7 were planted in outdoor plots to assess the impact of the dosage of fertilizer on biomass and saponin profile over 8 months.

The young plants were manually transplanted to outdoor plots at a plantation density of 50,000 plants per hectare. The planting and irrigation procedure was the same employed in the Example 8. The fertilizers were supplied in early summer after 3 months of growth, nitrogen supplied as urea, phosphorus supplied as triple superphosphate, and supplied as potassium magnesium sulfate. The dosages of fertilizers are summarized in Table 6. The morphological attributes of the plants are summarized in Table 7.

TABLE 6

Fertilizers Tested in an Ultrahigh-density Plantation (50,000 plants/hectare)

| Dosage of fertilizer | Nitrogen [Kg/Ha] | Phosphorus as $P_2O_5$ [Kg/Ha] | Potassium as $K_2O$ [Kg/Ha] |
|---|---|---|---|
| DF1 | 0 | 0 | 0 |
| DF2 | 150 | 100 | 150 |
| DF3 | 200 | 100 | 200 |
| DF4 | 250 | 100 | 250 |

TABLE 7

Morphology of Plants after Treatment with DF1, DF2, DF3, or DF4

| Dosage of fertilizer | Height [cm] | Diameter [cm] | Dry mass leaves/plant [g/plant] | Dry mass stem and twigs/plant [g/plant] | Dry mass aerial biomass/plant [g/plant] |
|---|---|---|---|---|---|
| DF1 | 69.4 | 8.6 | 24.2 | 24.9 | 49.1 |
| DF2 | 75.2 | 10.2 | 29.4 | 35.2 | 64.6 |
| DF3 | 78.7 | 10.1 | 30.7 | 27.7 | 58.4 |
| DF4 | 65.6 | 8.6 | 25.3 | 24.4 | 49.7 |

The saponin content in samples of leaf and twig biomass was determined according to the chromatographic procedure described in the Example 8. The yields of biomass and saponins after 8 months of growth and treatment with DF1, DF2, DF3 and DF4 are summarized in Table 8.

TABLE 8

Biomass and Saponin Yield

| Dosage of fertilizer | Dry mass leaves [Kg/Ha] | Dry mass stem and twigs [Kg/Ha] | Dry mass aerial biomass [Kg/Ha] | Saponins (leaves) [Kg/Ha] | Saponins (stem and twigs) [Kg/Ha] | Saponins (aerial biomass) [Kg/Ha] |
|---|---|---|---|---|---|---|
| DF1 | 1,211 | 1,243 | 2,454 | 81 | 33 | 114 |
| DF2 | 1,471 | 1,758 | 3,229 | 82 | 43 | 125 |
| DF3 | 1,533 | 1,385 | 2,918 | 122 | 67 | 189 |
| DF4 | 1,265 | 1,218 | 2,483 | 103 | 54 | 157 |

Example 9

Long-Term Quillaja Plantation Saponin Profiles

Young *Quillaja saponaria* Molina plants were planted at approximately 50,000 plants per hectare (ultrahigh-density) in outdoor plots as described in the Example 7. DE3 fertilizer was supplied according to Table 6. Samples of twigs and leaves were taken after one, three and four years of growth on the plantation for saponin analysis, as described in Example 9.

For comparison purposes, young plants of *Quillaja sapanaria* Molina were planted at approximately 2,500 plants per hectare (medium-density) in irrigated outdoor plots without fertilization. Samples of leaves and twigs were taken after three years of growth on the plantation for saponin analysis, as described in the Example 2.

Each sample taken above was analyzed according to the procedure described in the Example 2. The results for samples taken on the ultrahigh density plantation are summarized in Table 9.

TABLE 9

Saponin Content in Quillaja Biomass from an Ultrahigh Density Plantation

| Years on plantation | No. Plants Sampled (Leaf) | No. Plants Sampled (Twig) | Avg. Leaf Saponin Content [% w/w] on dry basis | Avg. Twig Saponin Content [% w/w] on dry basis |
|---|---|---|---|---|
| 0[a] | — | — | N/A | 1.6% |
| 1 | 80 | 80 | 8.28 +/− 2.31 | 5.63 +/− 1.85 |
| 3 | 21 | 128 | 7.84 +/− 1.16 | 4.78 +/− 2.45 |
| 4 | 30 | 30 | 7.72 +/− 2.18 | 3.39 +/− 0.76 |

[a]denotes averages for non-plantation plants

The saponin content in all plantation samples was substantially higher than the reported average value for both leaves and branches harvested from mature non-plantation *Quillaja* trees. The comparison between saponin contents of *Quillaja* biomass grown on ultrahigh and medium-density plantations (after 3 years) is summarized in Table 10. The saponin yields per hectare on ultrahigh and medium-density plantations are summarized in Table 11.

TABLE 10

Saponin Content from Ultrahigh and Medium-Density Quillaja Plantations

| Type of Plantation | No. Plants Sampled (Leaf) | No. Plants Sampled (Twig) | Avg. Leaf Saponin Content [% w/w] on dry basis | Avg. Twig Saponin Content [% w/w] on dry basis |
|---|---|---|---|---|
| Ultrahigh density | 21 | 128 | 7.84 | 4.78 |
| Medium density | 18 | 18 | 4.63 | 2.63 |

TABLE 11

Saponin Yield per Hectare

| Type of Plantation | Plantation density [Plants/Hectare] | Avg. leaf biomass harvested/plant [Kg/Ha] | Avg. twig biomass harvested/plant [Kg/Ha] | Avg. Leaf Saponins [Kg/Ha] | Avg. Twig Saponins [Kg/Ha] |
|---|---|---|---|---|---|
| Ultrahigh density | 50,000 | 2,690 | 8,340 | 211 | 399 |
| Medium density | 2,500 | 100 | 1,100 | 4.63 | 29 |

Accordingly, the harvesting of young plants grown from ultrahigh-density plantations of *Quillaja saponaria* Molina after 3 years of growth is a highly convenient alternative to other schemes for the production of biomass intended for saponin production. Indeed, the cycling time of ultrahigh plantations of *Quillaja saponaria* Molina (3 years) is significantly shorter than cycling times of harvesting of bark from mature non-plantation *Quillaja* trees (at least 15 years).

Example 10

Harvesting Biomass from an Ultrahigh-Density Plantation

Four tons of aerial biomass from 3-year-old *Quillaja* plants in an ultrahigh-density plantation was harvested and air-dried in situ under shade for 18 days to reduce the total volume of the material. The moisture content of the air-dried biomass was 0.1 g/(g dry). The dried biomass was chipped, rendering a primary chipped biomass having a particle size >19 mm. The primary chipped biomass was further milled and fractioned to provide a coarse fraction enriched in twigs and a fine fraction enriched in leaves by screening with a 0.15 mm wire sieve (sieve openings ~2.5 mm). The coarse fraction enriched in twigs was further fractioned in a Ro-Tap test sieve shaker with the following sieves: 19.0, 12,5, 8.0, 5.6, 4.0, 2.8, 2.0, 1.4, 1.0 and 0.71 mm. The size distribution of the fractionated coarse fraction enriched in twigs is summarized in Table 12.

TABLE 12

Size Distribution of Coarse Fraction Enriched in Twigs

| Sieve opening ASTM E - 11/95 [mm] | Retained biomass [g] | % p/p | Average size [mm] |
|---|---|---|---|
| ≥12.5 | 48.4 | 3.1% | 0.39 |
| 8.0 | 137.1 | 8.8% | 0.71 |
| 5.6 | 320.6 | 20.7% | 1.16 |
| 4.0 | 283.5 | 18.3% | 0.73 |
| 2.8 | 356.5 | 23.0% | 0.64 |
| 2.0 | 205.9 | 13.3% | 0.27 |
| 1.4 | 140.5 | 9.1% | 0.13 |
| 1.0 | 38.3 | 2.5% | 0.02 |
| <1.0 | 19.1 | 1.2% | 0.00 |
| Total | 1549.8 | 100% | 4.05 |

Three composite pools of twig fractions were prepared by mixing of sieve fractions obtained from the fractionation of the coarse twig fraction: i) Small size pool: Mix of fractions retained in 2.8, 2.0, 1.4 and 1.0 mm sieves; ii) Medium size pool: Mix of fractions retained in 4.0 and 5.6 mm sieves, and; iii) Large size pool: Mix of fractions retained in 8.0 and 12.5 mm sieves.

Figure 10:
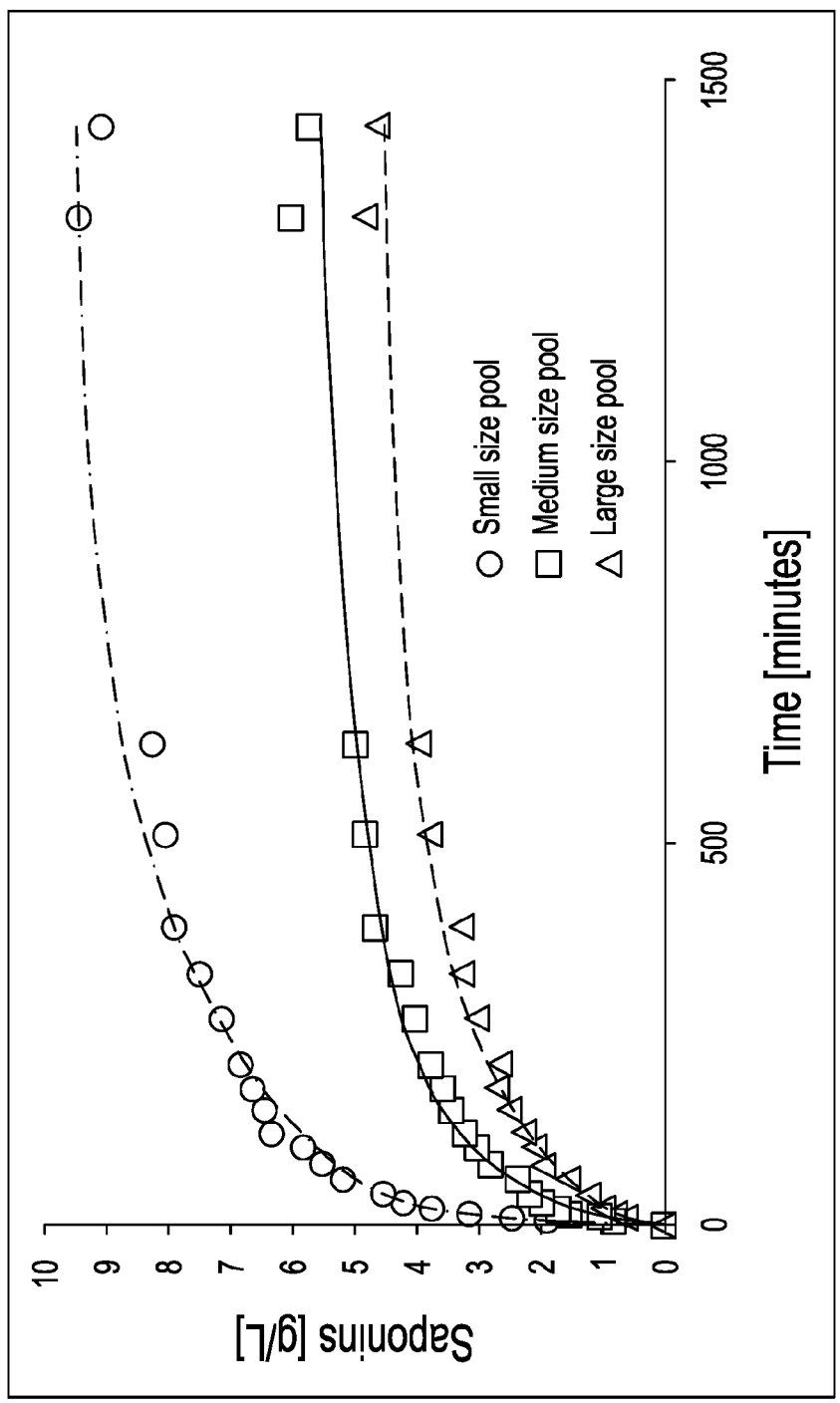
FIG. 10 depicts the saponin concentration profile in the extraction tests over time described in Example 10.

To characterize the kinetics of the leaching of saponins from each composite pool of twig fractions prepared above, extraction tests were performed at 70° C. A sample of each composite pool containing 150 g of dry biomass was mixed with 600 mL of water in a and the mixture was shaken for 24 hours, with 1.5 ml samples taken at 0, 5, 10, 15, 20, 30, 40, 60, 80, and 100 minutes, and 2 hours, 2.5 hours, 3 hours, 3.5 hours, 4.5 hours, 5.5 hours, 6.5 hours, 8.5 hours, 10.5 hours, 22 hours, and 24 hours for saponin analysis as described in the Example 8. The time profiles of saponin extraction are shown in FIG. 10. The concentrations of saponins in aqueous extracts obtained by extraction of composite pool of twig fractions at 1 hour, 2 hours, 6.5 hours, 10.5 hours, and 24 hours are summarized in Table 13.

TABLE 13

Saponin Content in Aqueous Extracts of Twig Fractions

| Extraction times [hr] | Saponin Conc. from Small Pool [g/L] | Saponin Conc. from Medium Pool [g/L] | Saponin Conc. from Large Pool [g/L] |
|---|---|---|---|
| 1 | 5.2 | 2.4 | 1.6 |
| 2 | 6.3 | 3.2 | 2.3 |
| 3 | 6.6 | 3.6 | 2.7 |
| 6.5 | 7.9 | 4.7 | 3.3 |
| 10.5 | 8.3 | 5.0 | 4.0 |
| 24 | 9.1 | 5.7 | 4.7 |

One or more of the individually-identified steps are contemplated as processes within the scope of this disclosure.

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A method of making an enriched saponin compositions, comprising:
   (i) selecting *Quillaja* sp. plants based on chromatographic analysis of aqueous extracts of plant biomass for chemotype or total R series of X series saponin content, wherein said plant biomass is selected from bark, trunk, leaves, stems, roots, seeds, flowers, fruits or a combination thereof; and wherein the selection comprises sampling *Quillaja* plant biomass, conducting an aqueous extraction of the plant biomass, analyzing the aqueous extracts of the sampled plant biomass by reversed phase HPLC or UHPLC chromatography, and selecting trees of a defined chemotype, X or R;
   (ii) removing axillary buds from said *Quillaja* sp. plants and inducing shoots of said axillary buds;
   (iii) growing apical meristems of the induced shoots to provide clone plantlets;
   (iv) growing said clone plantlets under controlled conditions to provide young plants;
   (v) transferring said young plants to an ultrahigh-density plantation;
   (vi) providing irrigation and nutrients to the young plants to provide young trees;
   (vii) harvesting the aerial biomass from the young trees;
   (viii) drying, grinding, and sieving said harvested biomass to provide biomass suitable for extraction:
   (ix) extracting said suitable biomass to provide an enriched saponin composition relative to that obtained from non-plantation biomass; and
   (x) repeating steps (vi)-(ix) about every year to about every 6 years.

2. The method of claim 1, wherein the *Quillaja* ,sp. is *Quillaja saponaria* Molina.

3. The method of any one of claims 1-2, wherein the ultrahigh-density plantation comprises from about 20,000 plants per hectare to about 100,000 plants per hectare.

4. A method of increasing the saponin content of *Quillaja* sp. plants, comprising:
   (i) selecting *Quillaja* sp. plants based on chromatographic analysis of aqueous extracts of plant biomass for chemotype or total R series or X series saponin content, wherein said plant biomass is selected from bark, trunk, leaves, stems, roots, seeds, flowers, fruits or a combination thereof; and wherein the selection comprises sampling *Quillaja* plant biomass, conducting an aqueous extraction of the plant biomass, analyzing the aqueous extracts of the sampled plant biomass by reversed phase HPLC or UHPLC chromatography, and selecting trees of a defined chemotype, X or R;
   (ii) removing axillary buds from said *Quillaja* sp. plants and inducing shoots of said axillary buds;
   (iii) growing apical meristems of the induced shoots to provide clone plantlets;
   (iv) growing said clone plantlets under controlled conditions to provide young plants;
   (v) transferring said young plants to an ultrahigh-density plantation;
   (vi) providing irrigation and nutrients to the young plants to provide young trees; and
   (vii) harvesting biomass from the young trees,
   wherein the biomass from said young trees has a higher saponin content than in non-plantation *Quillaja* sp. plants, and wherein the higher saponin content is selected from X-series saponins or R-series saponins.

* * * * *